US011961639B2

(12) United States Patent
Rajaraman et al.

(10) Patent No.: US 11,961,639 B2
(45) Date of Patent: Apr. 16, 2024

(54) MICROSERPENTINES AND ELECTRODES FOR STRETCHABLE AND CONFORMABLE BIOSENSOR APPLICATIONS

(71) Applicant: UNIVERSITY OF CENTRAL FLORIDA RESEARCH FOUNDATION, INC., Orlando, FL (US)

(72) Inventors: Swaminathan Rajaraman, Orlando, FL (US); Charles Didier, Orlando, FL (US); Avra Kundu, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 776 days.

(21) Appl. No.: 16/857,623

(22) Filed: Apr. 24, 2020

(65) Prior Publication Data

US 2020/0343018 A1    Oct. 29, 2020

Related U.S. Application Data

(60) Provisional application No. 62/838,620, filed on Apr. 25, 2019.

(51) Int. Cl.
*A61B 5/00*       (2006.01)
*H01B 7/06*       (2006.01)
*H05K 1/02*       (2006.01)

(52) U.S. Cl.
CPC ............. *H01B 7/06* (2013.01); *A61B 5/6801* (2013.01); *H05K 1/0283* (2013.01);
(Continued)

(58) Field of Classification Search
CPC ...... H01B 7/06; A61B 5/6801; A61B 2562/12; A61B 2562/164; A61B 5/25; A61B 5/291;
(Continued)

(56) References Cited

U.S. PATENT DOCUMENTS 10,154,583 B1 * 12/2018 Glickman ............ H05K 1/0281
2008/0039917 A1 * 2/2008 Cross .................. A61N 1/0551
607/122

(Continued)

OTHER PUBLICATIONS

Amjadi, Morteza et al., "Stretchable, Skin-Mountable, and Wearable Strain Sensors and Their Potential Applications: A Review", Adv. Funct. Materials, 2016, vol. 26, pp. 1678-1698.
(Continued)

*Primary Examiner* — Eugene T Wu
(74) *Attorney, Agent, or Firm* — Timothy H. Van Dyke; WOLTER, VAN DYKE, DAVIS, PLLC

(57) ABSTRACT

Various embodiments relate to a microserpentine including a plurality of u-bends, each having a degree of completeness ($\alpha$), in which an $\alpha$ value of 0° corresponds to a semi-circular shape, and in which an $\alpha$ value of +90° corresponds to a complete circle and −90° corresponds to a straight shape. Each of the plurality of u-bends may have an $\alpha$ value of from about −35° to about 45°. The microserpentine may include a core coated with a conductive coating. The core may include a polymeric material. Various embodiments relate to microelectronic devices and methods of producing the same. The microelectronic devices may include but are not limited to a microelectrode array, a microelectronics packaging, an interconnect, a stretchable sensor, a wearable sensor, a wearable actuator, an in vitro sensor, an in vivo sensor, and combinations thereof.

9 Claims, 31 Drawing Sheets

(52) U.S. Cl.
CPC ..... *A61B 2562/12* (2013.01); *A61B 2562/164* (2013.01); *H05K 2201/0133* (2013.01)

(58) Field of Classification Search
CPC ..... A61B 5/296; A61B 5/24; A61B 2562/125; H05K 1/0283; H05K 2201/0133; H05K 1/0393; H05K 1/028
See application file for complete search history.

(56) References Cited

U.S. PATENT DOCUMENTS

| | | | | |
|---|---|---|---|---|
| 2012/0051005 | A1* | 3/2012 | Vanfleteren | H01L 24/81 29/854 |
| 2013/0333094 | A1* | 12/2013 | Rogers | A61B 34/76 340/407.1 |
| 2014/0022746 | A1* | 1/2014 | Hsu | H05K 1/0283 174/254 |
| 2016/0358849 | A1* | 12/2016 | Jur | H01L 27/16 |
| 2017/0257944 | A1* | 9/2017 | Robinson | H05K 3/103 |

OTHER PUBLICATIONS

Du, Ping et al., "Tunable electrical and mechanical responses of PDMS and polypyrrole nanowire composites", J. Phys. D: Appl. Phys., 2013, vol. 46, 8 pages.

Guvanasen, Gareth S. et al., "A Stretchable Microneedle Electrode Array for Stimulating and Measuring Intramuscular Electromyographic Activity", IEEE Transactions on Neural Systems and Rehabilitation Engineering, Sptember 207, vol. 25, No. 9, pp. 1440-1452.

Hopcroft, Matthew A., et al. "What is the Young's Modulus of Silicon?", Journal of Microelectromechanical Systems, Apr. 2010, vol. 19, No. 2, pp. 229-238.

Didier, Charles et al., "From 3D to 4D: Integration of 3D Printed Structures for Fabrication of Multifunctional 4D Biological Microsensors for Lab-On-a-Chip and Wearable Applications", Manuscript presented at 22nd International Conference on Miniaturized Systems for Chemistry and Life Sciences, Nov. 2018, Kaohsiung, Taiwan, 4 pages.

* cited by examiner

1mm

1mm

1mm

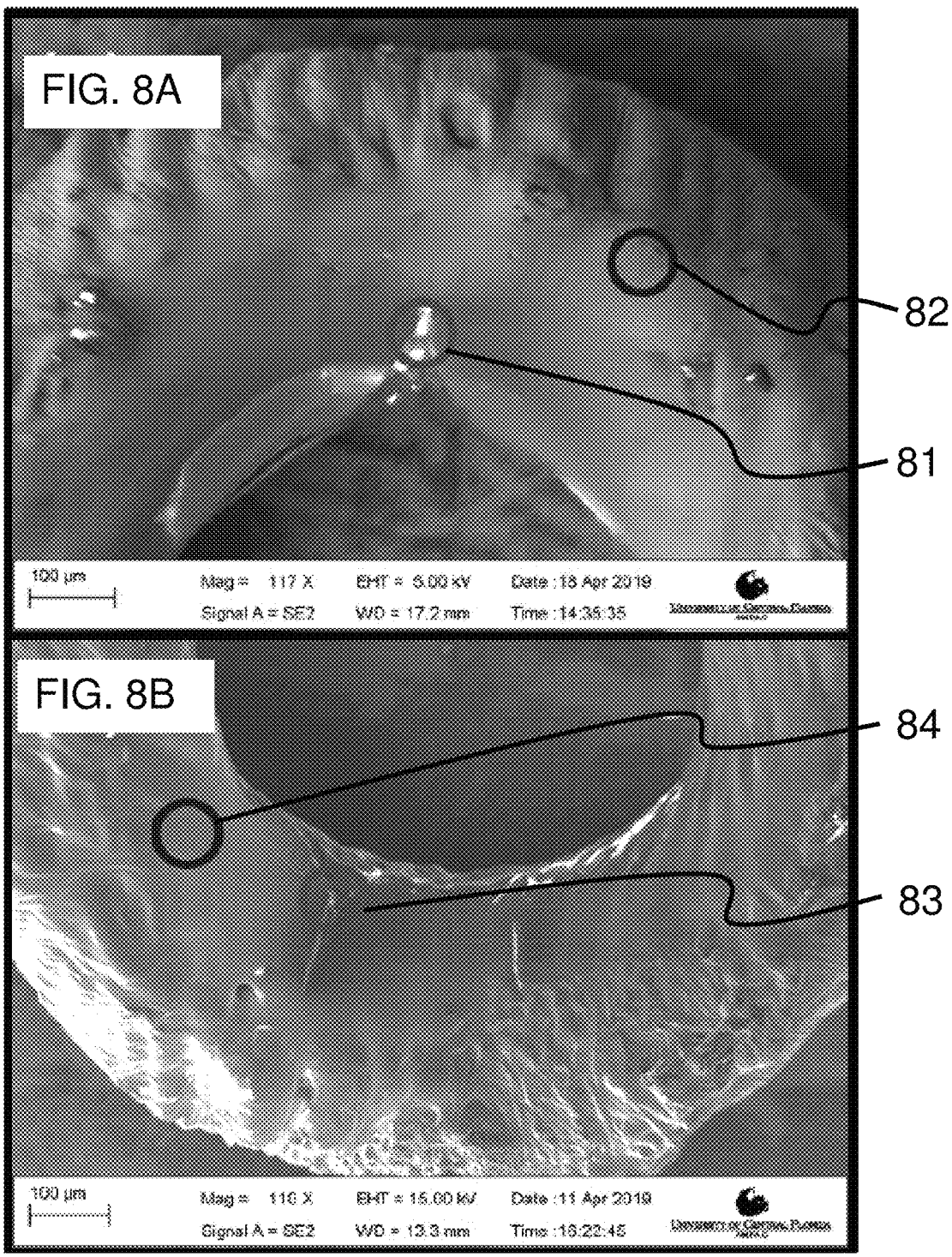

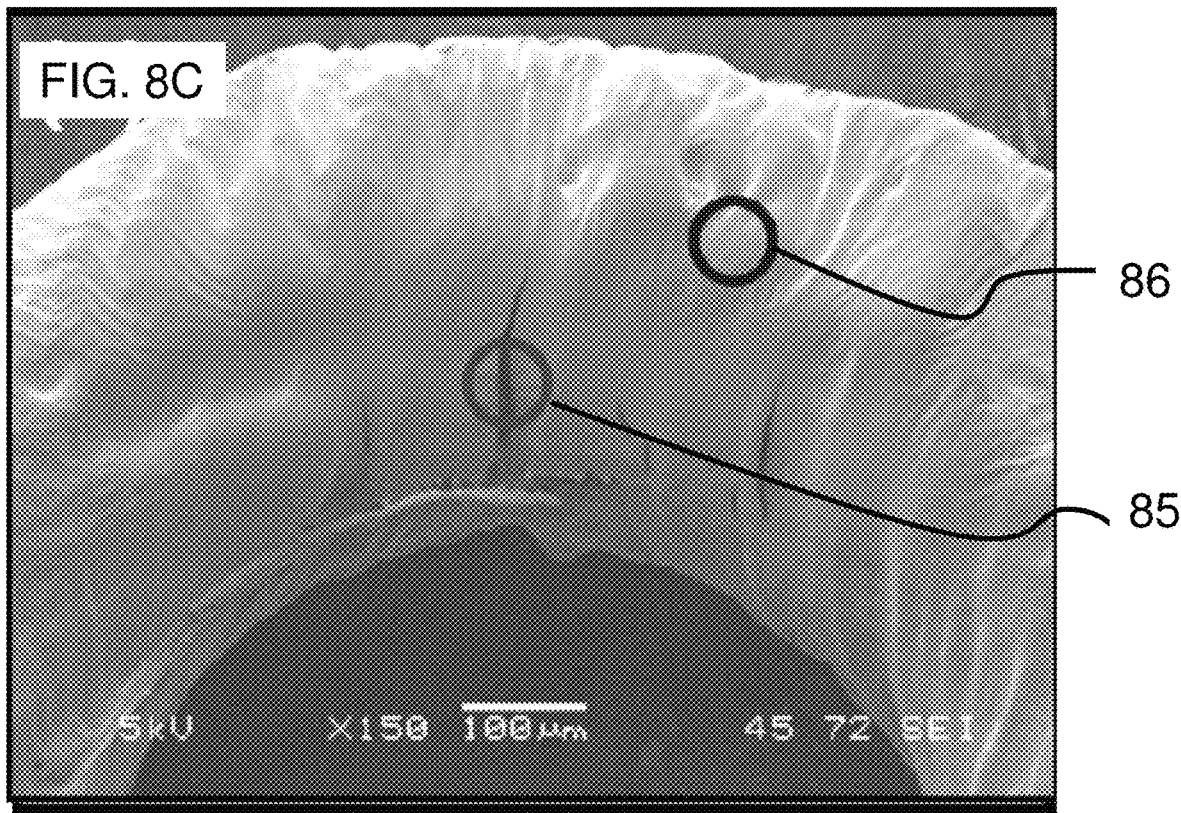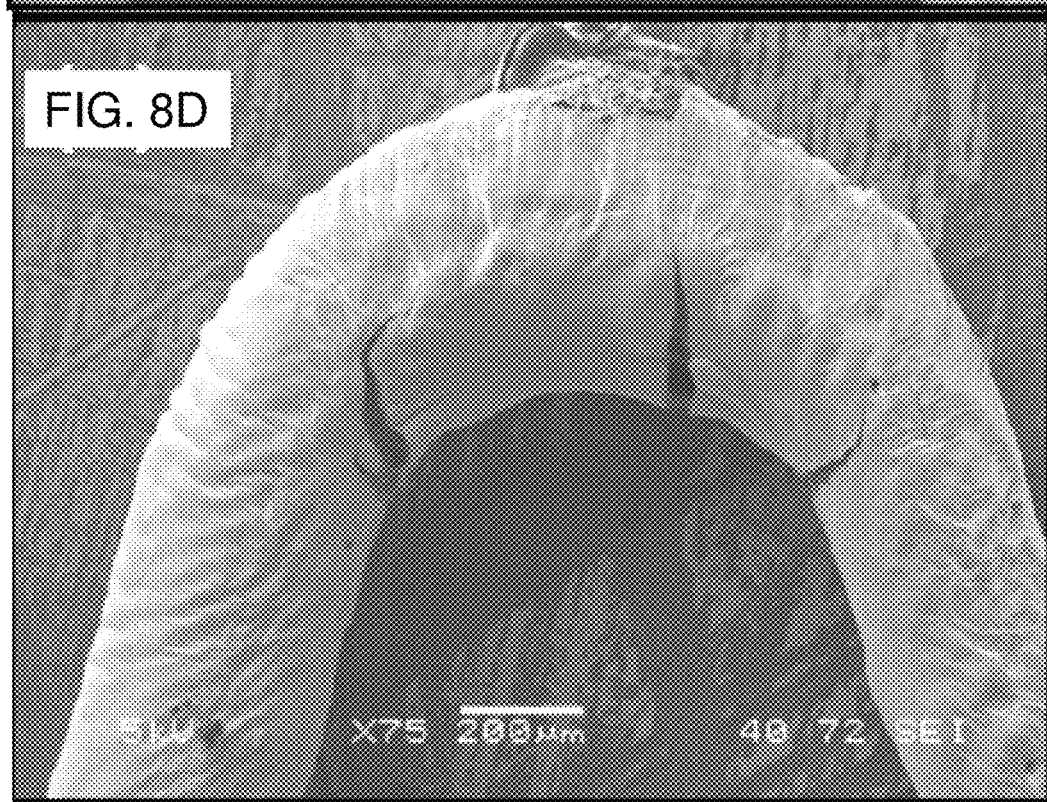

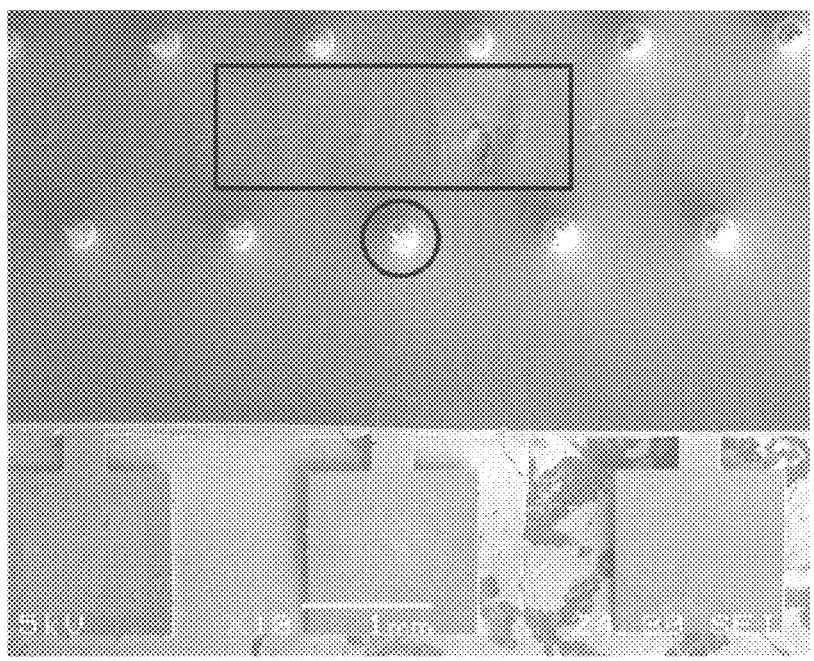
FIG. 14A
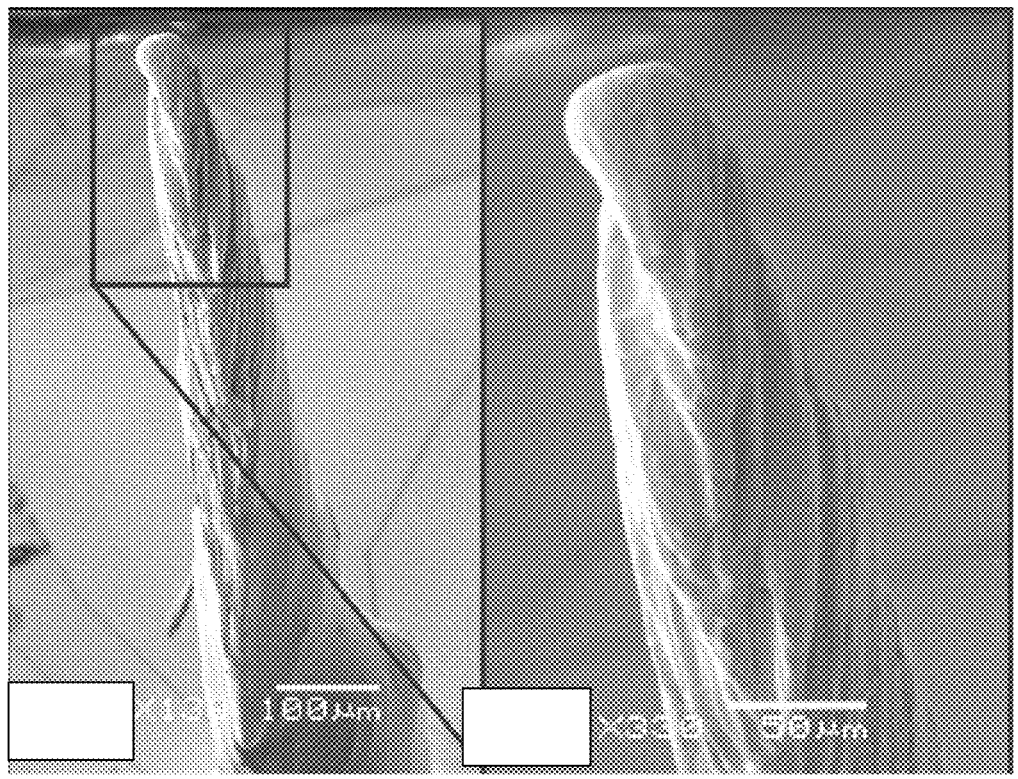
FIG. 14B                                                              FIG. 14C

| MEA Model | $R_s$ ($\Omega$) | $R_{CT}$ (k$\Omega$) | $C_{DL}$ (pF) | W (x$10^4$) (1/$\Omega_s^{-0.5}$) |
|---|---|---|---|---|
| Model Values | 180 | 3 | 10 | 9 |

MICROSERPENTINES AND ELECTRODES FOR STRETCHABLE AND CONFORMABLE BIOSENSOR APPLICATIONS

CROSS-REFERENCE TO RELATED APPLICATION

This application claims the benefit of U.S. Provisional Patent Application No. 62/838,620, filed Apr. 25, 2019, titled 4D BIOSENSORS AND METHODS FOR PRODUCING THE SAME, which is incorporated by reference herein in its entirety.

BACKGROUND

Stretchable electronics and microsensors have begun to be applied to several consumer and biomedical areas including wearables for personal health monitoring, surgical robotics, implantable devices, tactile sensors and devices for power harvesting and storage. A basic requirement in the microstructuring of such devices is the design and development of the components of the system able to deform mechanically without losing their ability to function electrically. Inorganic materials used in the microfabrication of stretchable microsensors such as silicon, and aluminum are very stiff and deform to an extent where electrical failure occurs at small amounts of tensile strain. In order to alleviate this problem, a common strategy for a device design with such materials, is to replace "straight wire" features fabricated out of these materials, with shapes engineered to be stretchable and flexible including "Archimedean spiral", "microserpentines" and other geometries. Specifically in flexible electronics devices, "serpentine" designs have resulted in enhanced strain performance. In addition to the aforementioned standard materials, there are numerous materials sets and combinations currently in use for the fabrication of stretchable electronics, with Polydimethylsiloxane (PDMS) being a widely used substrate and packaging material.

A common structure in a stretchable electronics system is a microelectrode which may include a substrate (with an additional package or the package defined on the substrate) atop which a grid or line of metal traces and an insulation layer are defined. Such two dimensional (2D) and 3D Microelectrode Arrays (MEAs) have become ubiquitous for in vitro, cell-based biosensing, wearable, implantable and environmental sensing applications.

Recently, the ease of microfabrication of complex shapes such as microserpentines and base structures for 2D and 3D MEAs has been achieved through rapid and cost effective additive manufacturing methods like 3D printing. Due to the commercial availability of various 3D printing systems, and the innovations of makerspace environments, the development of 3D printed devices has increasingly expanded and continues to show promise in innovation. While prior work, demonstrating the development of 2D and 3D MEAs in static cell culture settings has been reported, to date understanding the capabilities and limitation of 3D printed geometries and their application to stretchable and dynamic 3D microelectrodes is missing.

A need exists for microserpentines having new configurations, compositions, and properties, as well as for methods of producing such microserpentines and devices including such microserpentines.

BRIEF SUMMARY

Various embodiments relate to a microserpentine comprising a plurality of u-bends, each having a degree of completeness ($\alpha$), wherein an $\alpha$ value of 0° corresponds to a semi-circular shape, and wherein an $\alpha$ value of +90° corresponds to a complete circle and −90° corresponds to a straight shape, wherein each of the plurality of u-bends has an $\alpha$ value of from about −35° to about 45°. According to various embodiments, the microserpentine may have had an I/R ratio of about 2, and an $\alpha$ of about 10°, creating a microserpentine that could stretch up to about 155% its resting length. The microserpentine may comprise a core coated with a conductive coating.

The core may comprise a polymeric material. According to various embodiments, the polymeric material may comprise one selected from a methacrylate-based polymer, a urethane-based polymer, a styrene-based polymer, a siloxane-based polymer, a nitrile-based polymer, a block co-polymer, a hydrogel-based polymer, a fluoro-elastomer-based polymer, and combinations thereof. The polymeric material may have a Young's Modulus of about 5 kPa to about 130 GPa. The polymeric material may have a Poisson's ratio of about 0.1 to about 0.5.

According to various embodiments, the conductive coating may comprise one selected from a metallic material, a conductive polymer, a conductive polymer composite, and combinations thereof. The conductive coating may comprise a metallic material selected from gold, palladium, titanium, magnesium, zinc, platinum, and combinations thereof. The conductive coating may comprise a conductive polymer selected from a poly(fluorene), a polyphenylene, a polypyrene, a polyazulene, a polynaphthalene, a poly(acetylene) (PAC), a poly(p-phenylene vinylene) (PPV), a poly(pyrrole) (PPY), a polycarbazole, a polyindole, a polyazepine, a polyaniline (PANI), a poly(thiophene) (PT), a poly(3,4-ethylenedioxythiophene) (PEDOT), a poly(p-phenylene sulfide) (PPS), and combinations thereof. The conductive coating may comprise a conductive polymer composite selected from a carbon-based conductive polymer composite, a silver-based conductive polymer composite, a platinum-based conductive polymer composite, and combinations thereof. The conductive coating may be about 5 nm to about 300 µm thick.

Various embodiments relate to a microelectronic device comprising a microserpentine according to any of the various embodiments. The microelectronic device may be any type of microelectronic device. For example, according to various embodiments, the microelectronic device may be selected from a microelectrode array, a microelectronics packaging, an interconnect, a stretchable sensor, a wearable sensor, a wearable actuator, an in vitro sensor, an in vivo sensor, and combinations thereof.

Various embodiments relate to a microelectronic device comprising a microserpentine; a substrate; at least one microelectrode; and an insulating layer. The microserpentine may be disposed on the substrate. The at least one microelectrode may extend from the microserpentine. The at least one microelectrode may have the same composition as the microserpentine or a different composition than the microserpentine. The insulating layer may be disposed on at least the microserpentine. The microserpentine may comprise a core coated with a conductive coating. The microserpentine may comprise a plurality of u-bends, each having a degree of completeness ($\alpha$), wherein an $\alpha$ value of 0° corresponds to a semi-circular shape, and wherein an $\alpha$ value of +90° corresponds to a complete circle and −90° corresponds to a straight shape, and wherein each of the plurality of u-bends has an $\alpha$ value of from about −35° to about 45°.

According to various embodiments, the core may comprise a polymeric material. According to various embodiments, the conductive coating comprises one selected from a metallic material, a conductive polymer, a conductive polymer composite, and combinations thereof. According to various embodiments, the substrate may comprise one selected from a polyimide, a polyethylene terephthalate (PET), a polycarbonate (PC), a cyclic olefin copolymer (COC), a cyclic olefin polymer (COP), a polyethylene naphthalate (PEN), a poly(methyl methacrylate) (PMMA), a parylene, and combinations thereof. The substrate may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof. The insulating layer may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof.

The microelectronic device is selected from a microelectrode array, a microelectronics packaging, an interconnect, a stretchable sensor, a wearable sensor, a wearable actuator, an in vitro sensor, an in vivo sensor, and combinations thereof.

Various embodiments relate to a method of producing a microelectronic device, the method may comprise: producing a core via an additive manufacturing deposition to form a microserpentine, wherein the microserpentine comprises a plurality of u-bends, each having a degree of completeness ($\alpha$), wherein an $\alpha$ value of 0° corresponds to a semi-circular shape, and wherein an $\alpha$ value of +90° corresponds to a complete circle and −90° corresponds to a straight shape, wherein each of the plurality of u-bends has an $\alpha$ value of from about 5° to about 15°; placing the core onto a substrate; depositing at least one microelectrode onto the microserpentine; depositing a conductive coating on the microserpentine and the substrate; and depositing an insulating coating on the microserpentine and the substrate.

According to various embodiments, the core may comprise a polymeric material. The conductive coating may comprise one selected from a metallic material, a conductive polymer, a conductive polymer composite, and combinations thereof. The substrate may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof. The insulating layer may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof.

These and other features, aspects, and advantages of various embodiments will become better understood with reference to the following description, figures, and claims.

BRIEF DESCRIPTION OF THE FIGURES

Many aspects of this disclosure can be better understood with reference to the following figures, in which:

FIG. 8A: is an example according to various embodiments illustrating SEM and associated EDS data for analysis of an Au coating thickness of 20 nm after the application of uniaxial strain, in which circle 81 and circle 82 indicate points where EDS analysis was performed, with circle 81 being inside a fracture point, and circle 82 being outside a fracture point;

FIG. 8B: is an example according to various embodiments illustrating SEM and associated EDS data for analysis of an Au coating thickness of 33 nm after the application of uniaxial strain, in which circle 83 and circle 84 indicate points where EDS analysis was performed, with circle 83 being inside a fracture point, and circle 84 being outside a fracture point;

FIG. 8C: is an example according to various embodiments illustrating SEM and associated EDS data for analysis of an Au coating thickness of 70 nm after the application of uniaxial strain, in which circle 85 and circle 86 indicate points where EDS analysis was performed, with circle 85 being inside a fracture point, and circle 86 being outside a fracture point;

FIG. 8D: is an example according to various embodiments illustrating an SEM image of a separate 70 nm thick Au coating on a microserpentine after the application of strain, demonstrating much large fracturing of the Au film;

FIG. 14A: is an example according to various embodiments illustrating an SEM image of the fully assembled device, in which the highlighted regions denote where the laser isolation trace is located beneath the PDMS layer (and hence are difficult to visualize), and where the exposed circular electrode tips emerge from the PDMS layer;

FIG. 14B: is an example according to various embodiments illustrating an SEM image of the exposed electrode tip, in which, after insulation, it is estimated that the electrode tips are 300 μm in height above the surface of the PDMS;

FIG. 14C: is an example according to various embodiments illustrating an SEM close-up of the electrode tip from FIG. 14B, highlighting the naturally formed μSLA striations which contribute to the increased effective surface area of the 3D microelectrode;

It should be understood that the various embodiments are not limited to the examples illustrated in the figures.

DETAILED DESCRIPTION

Introduction and Definitions

Various embodiments may be understood more readily by reference to the following detailed description. Unless defined otherwise, all technical and scientific terms used herein have the same meaning as commonly understood by one of ordinary skill in the art to which this disclosure belongs.

As used herein, "microserpentine" refers to a microscale object having a serpentine shape.

As used herein, "microscale" refers to sizes or dimensions below about 1 mm. Each component of a microscale object has a size typically smaller than about 1 mm.

As used herein, "serpentine shape" refers to an external form or appearance characteristic that is winding, twisting, or zigzagging, like a snake. A serpentine shape may comprise one or more u-bends.

As used herein, "u-bend" refers to a twist or a zigzag in a serpentine shape via which the serpentine shape partially or completely doubles-back on itself.

As used herein, "degree of completeness ($\alpha$)" refers to a quantification of the extent to which a serpentine shape doubles-back on itself at a u-bend. An $\alpha$ value of 0° corresponds to a u-bend having a semi-circular shape, and an $\alpha$ value of +90° corresponds to a complete circle and −90° corresponds to a u-bend having a straight shape, as illustrated, for example, in FIG. 1B.

Figure 1A:
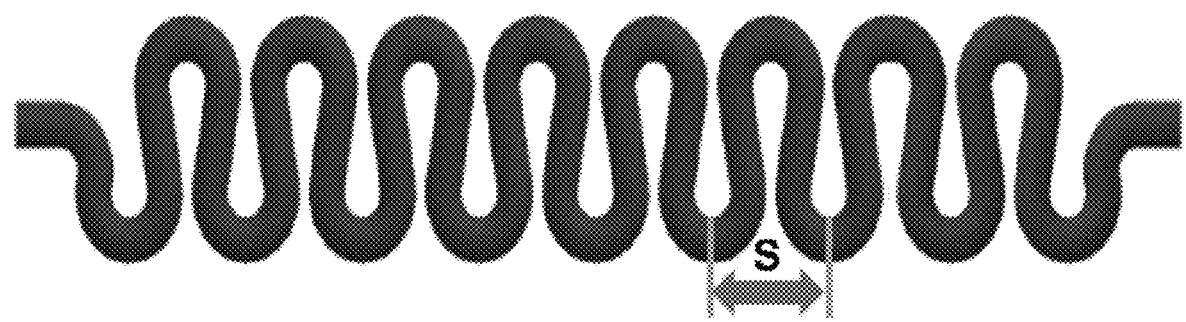
FIG. 1A: is an example according to various embodiments illustrating a schematic diagram of a microserpentine, illustrating various geometric features of the microserpentine, and denoting a singular "S" subunit of the microserpentine.
Figure 1B:
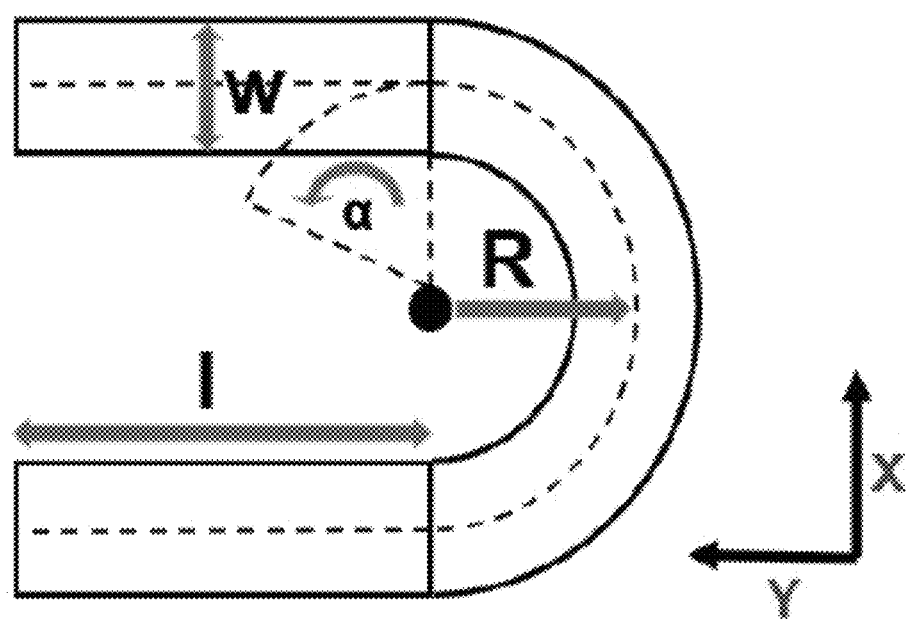
FIG. 1B: is an example according to various embodiments illustrating various geometric parameters of a microserpentine, and providing a reference orientation.

As used herein, the term "l" (lower-case letter "L") refers to the average length between u-bends in a serpentine shape as illustrated in FIG. 1B. Generally, the length between the u-bends in serpentine shapes manufactured via additive manufacturing techniques will be very uniform, but some variation is to be expected; hence, an average length is referenced.

As used herein, the term "R" refers to the average radius of a u-bend in a serpentine shape as illustrated in FIG. 1B. Generally, the radius of the u-bends in serpentine shapes manufactured via additive manufacturing techniques will be very uniform, but some variation is to be expected; hence, an average radius is referenced.

As used herein, the term "l/R" refers to the ratio of the length between u-bends and the radius of a u-bend in a serpentine shape as illustrated in FIG. 1B.

As used herein, "complete circle" means forming or shaped like a circle. It will be readily appreciated by those having ordinary skill in the art that a geometrically perfect circle is not required to meet the definition. A perfectly smooth arc is not required; for example, a complete circle may be formed by a plurality of straight segments. A complete circle may be formed primarily in two-dimensions, but according to various embodiments may also extend into a third-dimension.

As used herein, "semi-circular shape" means forming or shaped like a semicircle. It will be readily appreciated by those having ordinary skill in the art that a geometrically perfect semi-circle is not required to meet the definition. A perfectly smooth arc is not required; for example, a semi-circular shape may be formed by a plurality of straight segments. A semi-circular shape may be formed primarily in two-dimensions, but according to various embodiments may also extend into a third-dimension.

As used herein, "straight shape" means extending or shaped uniformly in one direction only; without a curve or bend. It will be readily appreciated by those having ordinary skill in the art that a geometrically perfect straight shape is not required to meet the definition. A perfectly linear shape is not required; for example, a straight shape may be formed by a plurality of segments each extending in slightly different directions as long as the overall shape extends uniformly in one direction only. A straight shape may be formed primarily in two-dimensions, but according to various embodiments may also extend into a third-dimension.

As used herein, "core" refers to the central part of an object.

As used herein, "conductive coating" refers to any layer that conducts electricity. The layer may be applied to a core.

As used herein, "polymeric material" refers to any material comprising a polymer.

As used herein, "polymeric composite" refers to any multi-phase material in which reinforcing fillers are integrated with a polymer matrix. The combination may result in synergistic mechanical properties that cannot be achieved from either component alone.

As used herein, "methacrylate-based polymer" refers to any polymer or copolymer that includes repeating methacrylate groups or that is derived from a methacrylate monomer, such as, for example, an acrylate polymer.

As used herein, "urethane-based polymer" refers to any polymer or copolymer that may refer to any polymer that includes repeating carbamate groups or urethane links, such as, for example, a polyurethane.

As used herein, "styrene-based polymer" refers to any polymer or copolymer that is derived from a styrene monomer, such as, for example, a polystyrene.

As used herein, "siloxane-based polymer" refers to any polymer or copolymer that includes repeating units of siloxane, such as, for example, polysiloxane.

As used herein, "nitrile-based polymer" refers to any polymer or copolymer that includes repeating nitrile groups.

As used herein, "copolymer" refers to a polymer derived from more than one species of monomer As used herein, "block co-polymer" refers to a copolymer that comprises two or more homopolymer subunits linked by covalent bonds.

As used herein, "hydrogel-based polymer" refers to any polymer or copolymer that includes a network of polymer chains that are hydrophilic. Hydrogels may include physical and/or chemical cross-links that impart structural integrity to the hydrogel network by holding the hydrophilic polymer chains together even when the hydrogel absorbs water.

As used herein, "fluoro-elastomer-based polymer" refers to any fluorocarbon-based synthetic rubber. Several compositions of fluroelastomers exist including, for example, FKM (by ASTM D1418 standard, equivalent to FPM by ISO/DIN 1629 standard); perfluoro-elastomers (FFKM); and tetrafluoro ethylene/propylene rubbers (FEPM).

As used herein, "Young's Modulus" refers to a standard measure of the stiffness of a solid material. It defines the relationship between stress (force per unit area) and strain (proportional deformation) in a material in the linear elasticity regime of a uniaxial deformation As used herein, "Poisson's ratio" refers to a standard measure of the Poisson effect, that describes the expansion or contraction of a material in directions perpendicular to the direction of loading.

As used herein, "metallic material" refers to a composition comprising a metal or a metalloid.

As used herein, "conductive polymer" refers to any polymer or copolymer that conducts electricity.

As used herein, "conductive polymer composite" refers to any polymer composite that conducts electricity.

As used herein, "carbon-based conductive polymer composite" refers to a conductive polymer composite comprising a filler that comprises carbon.

As used herein, "silver-based conductive polymer composite" refers to a conductive polymer composite comprising a filler that comprises silver.

As used herein, "platinum-based conductive polymer composite" refers to a conductive polymer composite comprising a filler that comprises platinum.

As used herein, "cyclic olefin copolymer (COC)" and "cyclic olefin polymer (COP)" refer to copolymers or polymers that contain, or are made from, at least one cyclic monomer.

As used herein, "parylene" refers to any polymer or copolymer manufactured from a p-xylylene intermediate. Parylenes include all chemical vapor deposited poly(p-xylylene) polymers or copolymers.

As used herein, "electrode" refers to an electrical conductor used to make contact with a nonmetallic part of a circuit.

As used herein, "microelectrode" refers to an electrode used in electrophysiology either for recording neural signals or for the electrical stimulation of nervous tissue, cardiac tissue, muscle tissue, retinal tissue, stem cells or any suitable tissue.

As used herein, "microelectrode array" (also referred to as multielectrode arrays) refers to a device that comprises multiple microelectrodes. Signals may be obtained or delivered through the microelectrodes, for example with respect to neural signals, essentially serving as neural interfaces that connect neurons to electronic circuitry. As already stated, electrical stimulation of nervous tissue, cardiac tissue, muscle tissue, retinal tissue, stem cells or any suitable tissue may be employed.

As used herein, "sensor" refers to a device, module, machine, or subsystem whose purpose is to detect events or changes in its environment and send the information to other electronics, frequently a computer processor.

As used herein, "microelectronics packaging" refers to any packaged micro electronic device or component.

As used herein, "interconnect" refers to a device used to connect electrically two things together.

As used herein, "stretchable sensor" refers to a sensor which can be used to measure deformation and stretching forces such as tension or bending.

As used herein, "wearable sensor" refers to a sensor that may be worn close to and/or on the surface of the skin, where they detect, analyze, and transmit information concerning e.g. body signals such as vital signs, and/or ambient data and which allow in some cases immediate biofeedback to the wearer As used herein, "wearable actuator" refers to a component that may be worn close to and/or on the surface of the skin and that is responsible for moving and controlling a mechanism or system.

As used herein, "in vitro sensor" refers to a sensor that is operated or positioned outside of an organism.

As used herein, "in vivo sensor" refers to a sensor that is operated or positioned within an organism.

As used herein, "substrate" refers to a base component comprising one or more materials onto which other components may be placed or deposited.

As used herein, "layer" refers to any deposition of molecules onto any substrate or component.

As used herein, "insulating layer" refers to a layer whose internal electric charges do not flow freely. Typically, very little electric current will flow through an insulating layer under the influence of an electric field.

As used herein, the term "standard temperature and pressure" generally refers to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent" or "mole percent" generally refers to the percentage that the moles of a particular component are of the total moles that are in a mixture. The sum of the mole fractions for each component in a solution is equal to 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

General Discussion

Various embodiments relate to the capabilities and limitations of 3D printed microserpentines and utilize these structures to develop dynamic 3D microelectrodes for potential applications for in vitro, wearable and implantable Microelectrode Arrays (MEAs). Devices according to various embodiments may incorporate optimized 3D printed microserpentine designs with out-of-plane microelectrode structures, integrated on to a flexible KAPTON® (a polyimide film developed in the late 1960s that remains stable across a wide range of temperatures, from −269 to +400° C.) package with micromolded PDMS insulation. The flexibility of the optimized, printed microserpentine design was calculated through effective stiffness and effective strain equations, to allow for analysis of various designs for enhanced flexibility. The optimized, down selected microserpentine design was further sputter coated with 7-70 nm thick gold and the performance of these coatings was studied for maintenance of conductivity during uniaxial strain application. Bending/conforming analysis of the final devices (3D MEAs with a KAPTON® package and PDMS insulation) were performed to qualitatively assess the robustness of the finished device toward dynamic MEA applications. 3D microelectrode impedance measurements varied from 4.2 to 5.2 kΩ during the bending process demonstrating a small change and an example application with artificial agarose skin composite model to assess feasibility for basic transdermal electrical recording was further demonstrated.

According to various embodiments, considerations and limitations for using standard and commercially available clear resin, to produce a stretchable and flexible engineered design that can incorporate robust 3D structures through additive micro-stereolithographic (µSLA) 3D printing is explored. Various embodiments have adapted and expanded on printed microserpentine structures. Similarly, the metallization of such 3D printed structures has not been fully characterized or understood. To demonstrate the benefits according to various embodiments metallized 3D printed microserpentines were analyzed for performance, reliability and bending/conformance.

Beyond the optimization of metallized microserpentines, 3D MEA devices according to various embodiments still require a package and an insulation. Materials such as polyimide (PI) and PDMS provide choices in polymeric backbone layers with improved mechanical match for dynamic biological tissue experiments (Young's Modulus of PI: 2.5 GPa, and PDMS: 360 kPa-2.97 MPa). Further, PDMS may be used in 2-2.5D flexible devices as both the substrate and the insulation material, because it also provides tunable mechanical and dielectric properties. According to various embodiments, PDMS may be used as an elastomeric insulation and thin KAPTON® polyimide has been used as a packaging substrate.

Various embodiments relate to the capabilities and limitations of 3D µSLA printed microserpentine for their applicability to 3D microelectrodes. Various embodiments integrate such metallized, microserpentines with a KAPTON® package and a PDMS insulated to develop a dynamic 3D Microelectrode Array (MEA). The microserpentines base structures used were optimized according to two key compound equations for the effective stiffness and maximum U-bend strain. According to various embodiments, the microserpentine may have had an I/R ratio of about 2, and an $\alpha$ of about 10°, creating a microserpentine that could stretch up to about 155% its resting length. This optimized microserpentine was subsequently characterized with varying conformal gold coating thicknesses, to find the optimal thickness to retain resistance values during strain. The resulting coating thickness was found to be 33 nm, and performed equally as well over twisting, and bending strain analyses, and with good reliability over 60 strain cycles. The final optimized and coated microserpentines structure was integrated into a device package build on polyimide (KAPTON®) substrates with metallized traces to connect to the laser isolated 3D microelectrode and encapsulated with PDMS insulation. The 3D microelectrode device was characterized for impedance and phase over a full frequency spectrum (10 Hz to 10 MHz), and the resulting electrophysiologically relevant 1 kHz values were measured for a dynamic MEA application: 4.2 kΩ (before bending), 4.6 kΩ (during bending), and 5.2 kΩ (after bending) respectively. This device was then employed to procure transdermal readings across an artificial agarose skin model, measuring the expected resistivity of 50 Ω-m. This details the capabilities, limitations and the versatility of µSLA printed serpentine-based 3D microstructures for various sensor devices with applications in wearable technologies, as well as dynamic cell culturing and in vitro conditions.

Various embodiments relate to a microserpentine comprising a plurality of u-bends, each having a degree of completeness ($\alpha$), wherein an $\alpha$ value of 0° corresponds to a semi-circular shape, and wherein an $\alpha$ value of +90° corresponds to a complete circle and −90° corresponds to a straight shape. The microserpentine may have a length (I) between each of the plurality of u-bends. Each of the plurality of u-bends may have a radius (R). According to various embodiments, each of the plurality of u-bends may have an $\alpha$ value of from about −35° to about 45°. Each range described herein is intended to include all numerical values encompassed by the range. Furthermore, additional ranges may be formed from any lower limits and/or upper limits described herein. For example, according to various embodiments, each of the plurality of u-bends may have an $\alpha$ value within a range having a lower limit and/or an upper limit. The range may include or exclude the lower limit and/or the upper limit. By way of example and not limitation, a lower limit and/or an upper limit may be selected from −35, −34, −33, −32, −31, −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 and 45°. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, according to various embodiments, each of the plurality of u-bends may have an α value of: about −35 to about 45°, less than about −35°, greater than about −35°, less than about 45°, or greater than about 45°, etc. All such ranges are contemplated and are intended to be explicitly disclosed and recited. Each value recited is intended to be modified by the term "about."

According to various embodiments, the microserpentine may have an I/R ratio of about 2. Each range described herein is intended to include all numerical values encompassed by the range. Furthermore, additional ranges may be formed from any lower limits and/or upper limits described herein. For example, according to various embodiments, the microserpentine may have an I/R ratio within a range having a lower limit and/or an upper limit. The range may include or exclude the lower limit and/or the upper limit. By way of example and not limitation, a lower limit and/or an upper limit may be selected from 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, and 10. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, according to various embodiments, the microserpentine may have an I/R ratio of: about 0.1 to about 3, less than about 0.1, greater than about 0.1, less than about 3, or greater than about 3, etc. All such ranges are contemplated and are intended to be explicitly disclosed and recited. Each value recited is intended to be modified by the term "about."

According to various embodiments, the microserpentine may be stretchable to about 155% its resting length. Each range described herein is intended to include all numerical values encompassed by the range. Furthermore, additional ranges may be formed from any lower limits and/or upper limits described herein. For example, the microserpentine may be stretchable to about within a range having a lower limit and/or an upper limit. The range may include or exclude the lower limit and/or the upper limit. By way of example and not limitation, a lower limit and/or an upper limit may be selected from 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 and 300% its resting length. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the microserpentine may be stretchable to about of: about 10 to about 300% its resting length, less than about 10% its resting length, greater than about 10% its resting length, less than about 300% its resting length, or greater than about 300% its resting length, etc. All such ranges are contemplated and are intended to be explicitly disclosed and recited. Each value recited is intended to be modified by the term "about."

According to various embodiments, the microserpentine may comprise a core coated with a conductive coating. The core may comprise a polymeric material. The core may comprise a polymeric composite, which implicitly includes a polymeric material. The polymeric material comprises one selected from a methacrylate-based polymer, a urethane-based polymer, a styrene-based polymer, a siloxane-based polymer, a nitrile-based polymer, a block co-polymer, a hydrogel-based polymer, a fluoro-elastomer-based polymer, and combinations thereof.

According to various embodiments, the polymeric material have a Young's Modulus of about 5 kPa to about 130 GPa. Each range described herein is intended to include all numerical values encompassed by the range. Furthermore, additional ranges may be formed from any lower limits and/or upper limits described herein. For example, the polymeric material has a Young's Modulus within a range having a lower limit and/or an upper limit. The range may include or exclude the lower limit and/or the upper limit. By way of example and not limitation, a lower limit and/or an upper limit may be selected from 5 kPa, 10 kPa, 100 kPa, 200 kPa, 300 kPa, 400 kPa, 500 kPa, 600 kPa, 700 kPa, 800 kPa, 900 kPa, 1 MPa, 10 MPa, 100 MPa, 200 MPa, 300 MPa, 400 MPa, 500 MPa, 600 MPa, 700 MPa, 800 MPa, 900 MPa, 1 GPa, 10 GPa, 100 GPa, 110 GPa, 120 GPa, 130 GPa, 140 GPa, 150 GPa, 160 GPa, 170 GPa, 180 GPa, 190 GPa, 200 GPa. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the polymeric material has a Young's Modulus of: about 5 kPa to about 130 GPa, less than about 5 kPa, greater than about 5 kPa, less than about 130 GPa, or greater than about 130 GPa, etc. All such ranges are contemplated and are intended to be explicitly disclosed and recited. Each value recited is intended to be modified by the term "about."

According to various embodiments, the polymeric material may have a Poisson's ratio of about 0.1 to about 0.5. Each range described herein is intended to include all numerical values encompassed by the range. Furthermore, additional ranges may be formed from any lower limits and/or upper limits described herein. For example, the polymeric material may have a Poisson's ratio within a range having a lower limit and/or an upper limit. The range may include or exclude the lower limit and/or the upper limit. By way of example and not limitation, a lower limit and/or an upper limit may be selected from 0.1, 0.15, 0.2, 0.25, 0.3, 0.35, 0.4, 0.45, 0.5, 0.55, 0.6, 0.65, 0.7, 0.75, 0.8. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the polymeric material may have a Poisson's ratio of: about 0.1 to about 0.8, less than about 0.1, greater than about 0.1, less than about 0.8, or greater than about 0.8, a Poisson's ratio of about 0.4, etc. All such ranges are contemplated and are intended to be explicitly disclosed and recited. Each value recited is intended to be modified by the term "about."

According to various embodiments, the conductive coating may comprise one selected from a metallic material, a conductive polymer, a conductive polymer composite, and combinations thereof. The conductive coating may comprise a metallic material selected from gold, palladium, titanium, magnesium, zinc, platinum, and combinations thereof. The conductive coating may comprise a conductive polymer selected from a poly(fluorene), a polyphenylene, a polypyrene, a polyazulene, a polynaphthalene, a poly(acetylene) (PAC), a poly(p-phenylene vinylene) (PPV), a poly(pyrrole) (PPY), a polycarbazole, a polyindole, a polyazepine, a polyaniline (PANI), a poly(thiophene) (PT), a poly(3,4-ethylenedioxythiophene) (PEDOT), a poly(p-phenylene sulfide) (PPS), and combinations thereof. The conductive coating may comprise a conductive polymer composite selected from a carbon-based conductive polymer composite, a silver-based conductive polymer composite, a platinum-based conductive polymer composite, and combinations thereof.

According to various embodiments, the conductive coating may have a thickness of about 5 nm to about 300 µm Each range described herein is intended to include all numerical values encompassed by the range. Furthermore, additional ranges may be formed from any lower limits and/or upper limits described herein. For example, the conductive coating may have a thickness within a range having a lower limit and/or an upper limit. The range may include or exclude the lower limit and/or the upper limit. By way of example and not limitation, a lower limit and/or an upper limit may be selected from 5 nm, 6 nm, 7 nm, 8 nm, 9 nm, 10 nm, 20 nm, 30 nm, 31 nm, 32, nm, 33 nm, 34 nm, 35 nm, 36 nm, 37 nm, 38 nm, 39 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 µm, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, and 300 µm. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, the conductive coating may have a thickness of: about 5 nm to about 300 µm, less than about 5 nm, greater than about 5 nm, less than about 300 µm, or greater than about 300 µm, etc. All such ranges are contemplated and are intended to be explicitly disclosed and recited. Each value recited is intended to be modified by the term "about."

Various embodiments relate to a microelectronic device comprising a microserpentine according to any of the embodiments described herein. The microelectronic device may be any microelectronic device, including but not limited to a microelectrode array, a microelectronics packaging, an interconnect, a stretchable sensor, a wearable sensor, a wearable actuator, an in vitro sensor, an in vivo sensor, and combinations thereof.

Various embodiments relate to a microelectronic device, such as a microelectrode device, comprising: a microserpentine; a substrate; at least one microelectrode; and an insulating layer, wherein the microserpentine is disposed on the substrate, wherein the at least one microelectrode extends from the microserpentine, wherein the insulating layer is disposed on at least the microserpentine.

The microelectronic device may be any microelectronic device, including but not limited to a microelectrode array, a microelectronics packaging, an interconnect, a stretchable sensor, a wearable sensor, a wearable actuator, an in vitro sensor, an in vivo sensor, and combinations thereof.

The microserpentine may be a microserpentine according to any of the embodiments described herein. Explicit recitation of all variations, configurations, and compositions of the microserpentine is omitted as duplicative. For example, the microserpentine may comprise a core coated with a conductive coating. Again, the core and the coating may have a configuration and compositions as already described with respect to any other embodiment. Explicit recitation of all variations, configurations, and compositions is omitted as duplicative. The microserpentine may comprise a plurality of u-bends, each having a degree of completeness ($\alpha$), wherein an $\alpha$ value of 0° corresponds to a semi-circular shape, and wherein an $\alpha$ value of +90° corresponds to a complete circle and −90° corresponds to a straight shape, wherein each of the plurality of u-bends has an $\alpha$ value of from about −35° to about 45°.

According to various embodiments, the substrate may comprise one selected from a polyimide, a polyethylene terephthalate (PET), a polycarbonate (PC), a cyclic olefin copolymer (COC), a cyclic olefin polymer (COP), a polyethylene naphthalate (PEN), a poly(methyl methacrylate) (PMMA), a parylene, and combinations thereof. The substrate may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof. According to various embodiments, the substrate may comprise polydimethylsiloxane.

According to various embodiments, the insulating layer may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof. The insulating layer may comprise polydimethylsiloxane.

Various embodiments relate to a method of producing a microelectronic device. The microelectronic device may be any microelectronic device, including but not limited to a microelectrode array, a microelectronics packaging, an interconnect, a stretchable sensor, a wearable sensor, a wearable actuator, an in vitro sensor, an in vivo sensor, and combinations thereof.

The method may comprise producing a core via an additive manufacturing deposition to form a microserpentine. The microserpentine may be a microserpentine according to any of the embodiments described herein. Explicit recitation of all variations, configurations, and compositions of the microserpentine is omitted as duplicative. For example, the microserpentine may comprise a core coated with a conductive coating. Again, the core and the coating may have a configuration and compositions as already described with respect to any other embodiment. Explicit recitation of all variations, configurations, and compositions is omitted as duplicative. The microserpentine may comprise a plurality of u-bends, each having a degree of completeness (α), wherein an α value of 0° corresponds to a semi-circular shape, and wherein an α value of +90° corresponds to a complete circle and −90° corresponds to a straight shape, wherein each of the plurality of u-bends has an α value of from about −35° to about 45°.

The method may further comprise placing the core that forms the microserpentine onto a substrate; depositing at least one microelectrode onto the microserpentine; depositing a conductive coating on the microserpentine and the substrate; and depositing an insulating coating on the microserpentine and the substrate. According to various embodiments, the substrate may comprise one selected from a polyimide, a polyethylene terephthalate (PET), a polycarbonate (PC), a cyclic olefin copolymer (COC), a cyclic olefin polymer (COP), a polyethylene naphthalate (PEN), a poly(methyl methacrylate) (PMMA), a parylene, and combinations thereof. The substrate may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof. According to various embodiments, the substrate may comprise polydimethylsiloxane. According to various embodiments, the insulating layer may comprise one selected from a urethane-based polymer, a styrene-based polymer, a siloxane-based polymer, a nitrile-based polymer, a block co-polymer, a hydrogel-based polymer, a fluoro-elastomer-based polymer, a parylene, and combinations thereof. The insulating layer may comprise polydimethylsiloxane.

Examples

Introduction

The following examples are put forth to provide those of ordinary skill in the art with a complete disclosure and description of how to perform the methods, how to make, and how to use the compositions and compounds disclosed and claimed herein. Efforts have been made to ensure accuracy with respect to numbers (e.g., amounts, temperature, etc.), but some errors and deviations should be accounted for. The purpose of the following examples is not to limit the scope of the various embodiments, but merely to provide examples illustrating specific embodiments.

FIG. 1A is an example according to various embodiments illustrating a schematic diagram of a microserpentine, illustrating various geometric features of the microserpentine, and denoting a singular "S" subunit of the microserpentine. FIG. 1B is an example according to various embodiments illustrating various geometric parameters of a microserpentine, and providing a reference orientation.

Figure 2A:
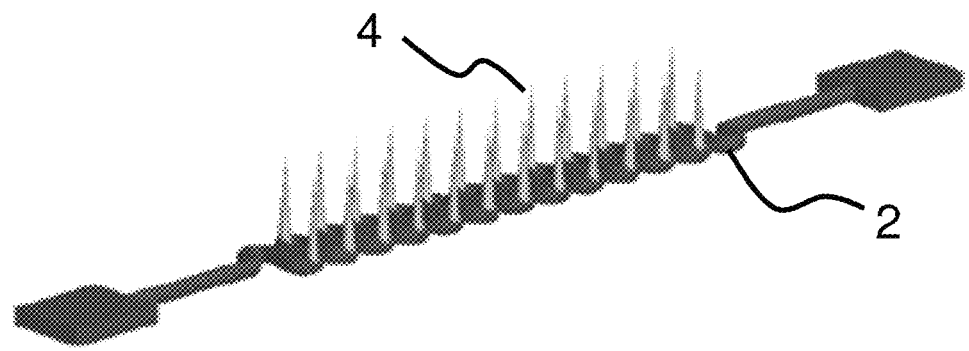
FIG. 2A: is an example according to various embodiments illustrating a schematic diagram showing one step of a process according to various embodiments, showing a 3D printed microserpentine with out of plane electrode structures.
Figure 2B:
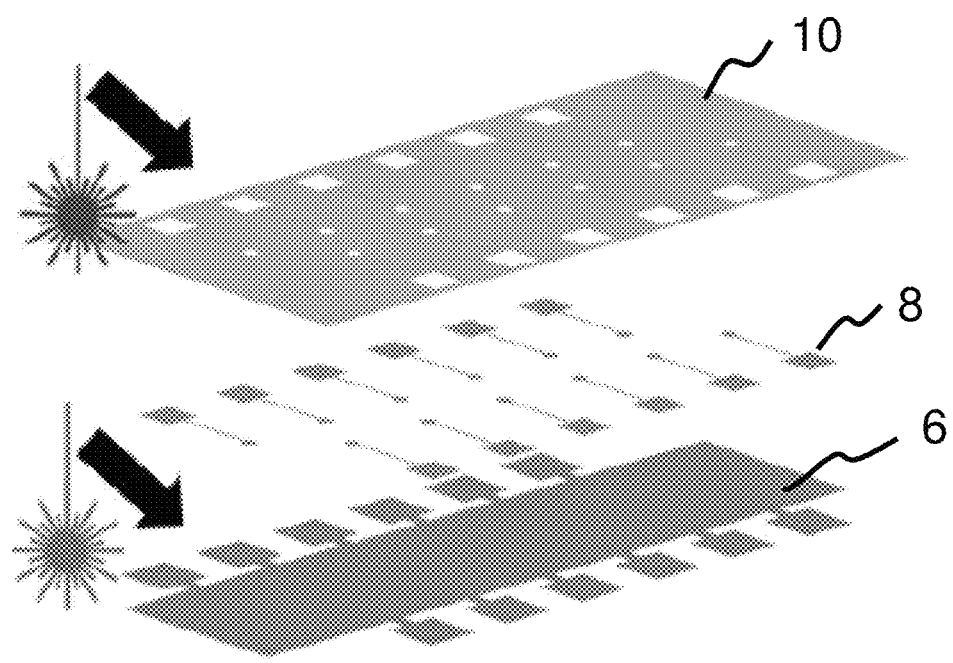
FIG. 2B: is an example according to various embodiments illustrating a schematic diagram showing one step of a process according to various embodiments, showing initial fabrication steps, including the UV laser micromachining of the KAPTON® substrate, and the IR laser micromachining of the steel deposition mask with associated sputter metallization of the Au traces.
Figure 2C:
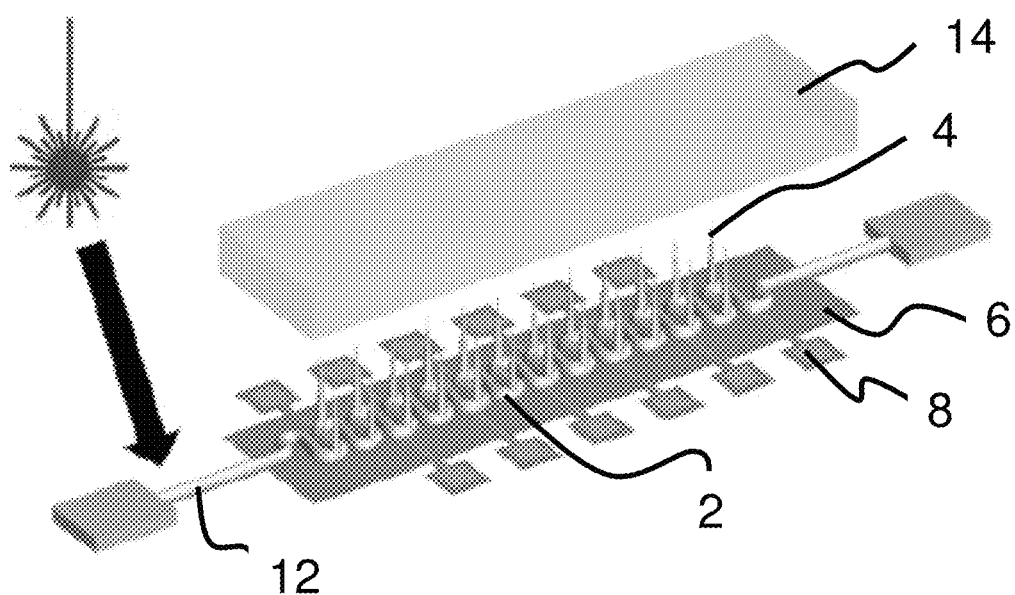
FIG. 2C: is an example according to various embodiments illustrating a schematic diagram showing one step of a process according to various embodiments, showing assembly of the full device, where a metallized microserpentine is IR laser micromachined selectively to isolate the electrodes, and then is placed on the KAPTON® package and insulated with PDMS.
Figure 2D:
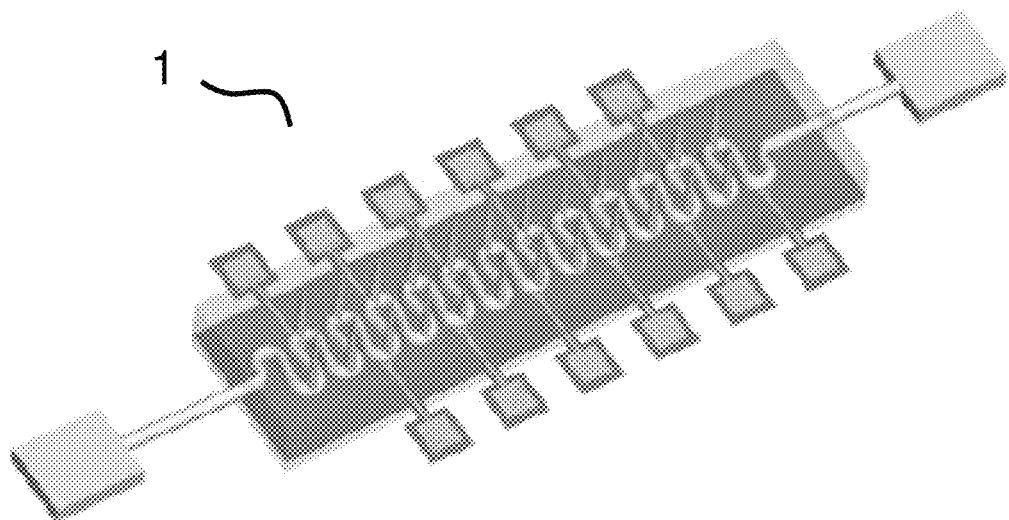
FIG. 2D: is an example according to various embodiments illustrating a schematic diagram showing a schematic of the fully assembled device, resulting from a process according to various embodiments.

One of many possible applications of the microserpentines according to various embodiments is a multielectrode array (MEA). A schematic for the microfabrication and packaging of a 3D MEAs is depicted in FIGS. 2A, 2B, 2C, and 2D. The stretchable, conformable 3D MEA was constructed with a singular microserpentine design and was subsequently electrically and mechanically characterized. An analytical model was developed for the design of the printed microserpentine structures. Further to demonstrate the potential applicability of devices according to various embodiments in biopotential measurements, puncture and conductivity characteristics on an artificial skin agarose model were explored. Various embodiments introduce a novel, flexible, rapidly fabricated and cost-effective packaging substrate that can be applied to a variety of flexible biosensor, wearable, implantable and cell/tissue culturing applications. FIG. 2A is an example according to various embodiments illustrating a schematic diagram showing one step of a process according to various embodiments, which may be useful for fabricating a variety of microelectronic devices, such as for example an MEA 1, showing a 3D printed microserpentine 2 with out of plane electrode structures 4. FIG. 2B is an example according to various embodiments illustrating a schematic diagram showing one step of the process, showing initial fabrication steps, including the UV laser micromachining of the KAPTON® substrate 6, and the IR laser micromachining of the steel deposition mask 10 with associated sputter metallization of the Au traces 8. FIG. 2C is an example according to various embodiments illustrating a schematic diagram showing one step of the process, showing assembly of the full device, where a metallized microserpentine 12 is IR laser micromachined selectively to isolate the electrodes, and then is placed on the KAPTON® package and insulated with PDMS 14. FIG. 2D is an example according to various embodiments illustrating a schematic diagram a schematic of a fully assembled device, which may be, for example, an MEA 1.

Two key equations (Equations 1 and 2) provide a useful foundation for analytically modeling microserpentine geometries and down-selecting 3D printing test structures according to various embodiments. These equations are based on plane-strain elastic theory and Winkler curved beam theory.

Equation 1 is the compound equation for the effective stiffness of a given microserpentine design:

$$\frac{PS}{2\bar{E}wu_0} = \frac{\left(\frac{w}{R}\right)*\left((\cos[\alpha]) - \left(\left(\frac{l}{(2R)}\right)\sin[\alpha]\right)\right)}{2\left[\left((\cos[\alpha]^2)\left(\frac{l^3}{(2R^3)}\right) + \left(3(\frac{\pi}{2}+\alpha)\right)\left(\frac{l^2}{R^2}\right)\right) + \left(12\left(\frac{l}{R}\right)\right) - 12(\frac{\pi}{2}+\alpha)\right) + \left(\sin[2\alpha]\left(\left(6(\frac{\pi}{2}+\alpha)\left(\frac{l}{R}\right)+9\right)\right)\right) + \left(\left(\left(\frac{w^2}{R}\right)(\frac{\pi}{2}+\alpha)\left(\frac{l}{2R}\cos[\alpha] + \sin[\alpha]\right)^2 + \left(\left(\frac{l}{2R}\right)\left(\sin[\alpha] + \left(\left(\frac{3\bar{E}}{2G}\right)\cos[\alpha]\right)\right)\right) + \left(18(\frac{\pi}{2})+\alpha\right)\right)\right]}$$ (1)

In this equation, "P" denotes the reaction force, "S" is the length of a given serpentine, "W" is the width of that serpentine, and "$2u_0$" is the effective displacement of the serpentine, giving rise to $PS/(2Ewu_0)$ on the left side of the equation, which is expanded on the right side.

Equation 2 is similarly the compound equation for the maximum effective strain on the inner U-bend curvature (FIG. 3B) of a given microserpentine design, and is expanded from $\varepsilon_{max}$ (the maximum tensile strain on the serpentine) and $\varepsilon_{applied}$ (the effective applied tensile strain):

$$\frac{\varepsilon[max]}{\varepsilon[app]} = \frac{\left(\sin[\alpha] + \left(\left(\frac{l}{2R}\right)\cos[\alpha]\right)\right)*\left(\left(\cos[\alpha] - \left(\left(\frac{l}{2R}\right)\sin[\alpha]\right)\right)\right)}{\left((\cos[\alpha])^2\right)\left(\left(\frac{l^3}{(2R^3)}\right) + \left(3\left(\frac{\pi}{2}+\alpha\right)\right)\left(\frac{l^2}{R^2}\right)\right) +} \left(\frac{w}{R}\right)\left(\left(\frac{12}{\left(2-\left(\frac{w}{R}\right)\right)}\right) + \left(\left(\left(\frac{12}{\left(2-\left(\frac{w}{R}\right)\right)}\right) - \left(\frac{w}{R}\right)\right)\right)\right) \quad (2)$$

(equation continues with terms including $\left(12\left(\frac{l}{R}\right)\right) - 12\left(\frac{\pi}{2}+\alpha\right)\right) + \left(\sin[2\alpha]\left(\left(6\left(\frac{\pi}{2}+\alpha\right)\left(\frac{l}{R}\right)+9\right)\right)\right) +$ ; $\left(\left(\left(\frac{w^2}{R}\right)\left(\frac{\pi}{2}+\alpha\right)\left(\frac{l}{(2R)}\right)\cos[\alpha]+\sin[\alpha]\right)^2 +$ ; $\left(\left(\frac{l}{2R}\right)\left(\sin[\alpha]+\left(\frac{3E}{2G}\right)\cos[\alpha]\right)\right) + \left(18\left(\frac{\pi}{2}\right)+\alpha\right)\right)$ )

Both equations were tabulated with respect to the specific aspects of a microserpentine interconnect geometry, as shown in FIG. 1B. In these equations, close attention needs to be devoted to the α value and the ratio of l/R.

The resin used for the device in this work was the clear (FLGPCL04) resin from FORMLABS®. This material is inherently inflexible but could resolve the necessary structures to create 3D electrodes to be used in the final device and as a result was chosen as the material for 3D printing. The plane strain modulus of the resin material is denoted as "E," and the shear modulus of the resin material is denoted as "G." These values were calculated using the Young's Modulus of the FORMLABS® Form 2 Clear resin at 2.8 GPa, and Poisson's Ratio of 0.4 (Poly(methyl methacrylate): PMMA), which is the closest approximation available for the resin, since it is largely proprietary, but is known to be Methacrylate-based.

The α values denote the degree of completeness of the central arc of the semi-circle of the microserpentine U-bend, with respect to a standard semi-circle (has an α value of 0°). All values of a are denoted in one quadrant of the central circular arc length and are reflected bilaterally across the semi-circle. The positive values of a denote a circle closer to completion. An α value of 0° being a standard semi-circle, and an α of 90° being a completed circle. Values of a below 0°, denote a less than complete circle, and thus the structure would reach a flat and straight ribbon at an α of −90°. The length "l" is the distance between the U-bends of the microserpentine interconnects, and the ratio of this length to the radius "R" of the U-bend's semi-circle, is an important distinction for the distribution of strains as the microserpentine is stretched. The width "w" was fixed for this analytical calculation at an experimentally defined value of 400 μm. This was the smallest dimension that the Form 2 μSLA 3D printer could resolve in this configuration, because of the need for printing support structures. Similarly, the value of "R" was fixed at 400 μm to ensure maximum printability given the previous width constraint. It should be noted, that because of the microserpentine's circular profile in this experimental setup, the thickness and the width were set as equivalent, which differs from a mathematical setup in which the microserpentines are printed to have a rectangular cross-sectional profile, leading to differing width and thickness. The singular subunit for a given microserpentine design is also illustrated in FIG. 1A, as denoted by "S."

Figure 3A:
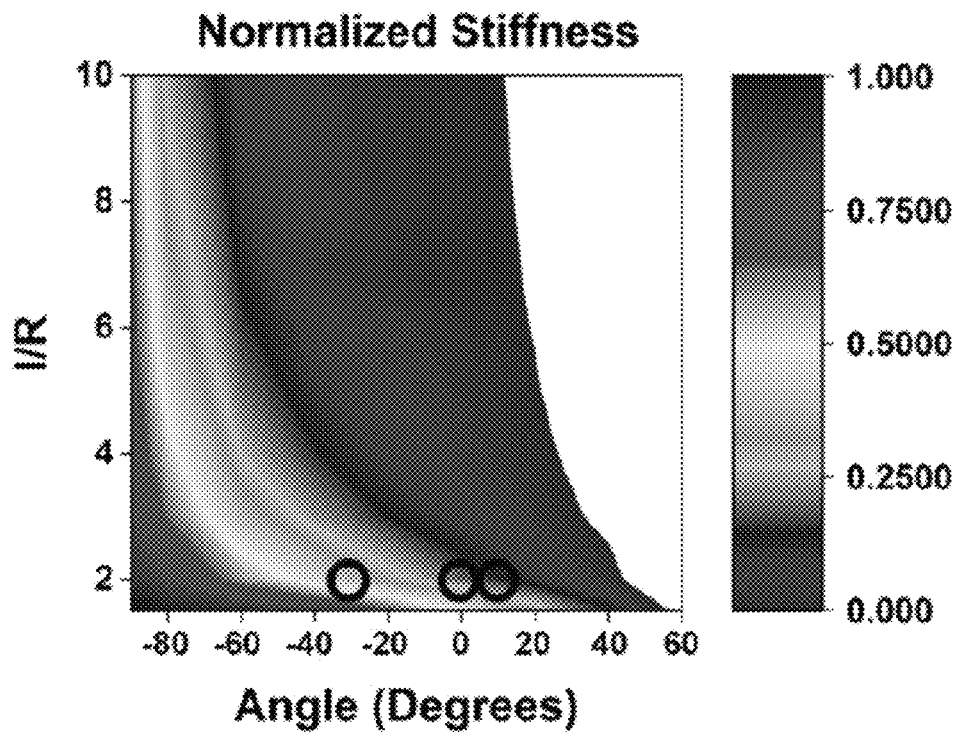
FIG. 3A: is an example according to various embodiments illustrating a contour plot of the normalized stiffness for a microserpentine (with FORMLABS® Clear resin) calculated from the analytical model developed using Equation 1, in which the hotter colors denote conformation closer to the stiffness of a flat ribbon (where $\alpha=-90°$), and in which circles indicate the design choices according to various examples.
Figure 3B:
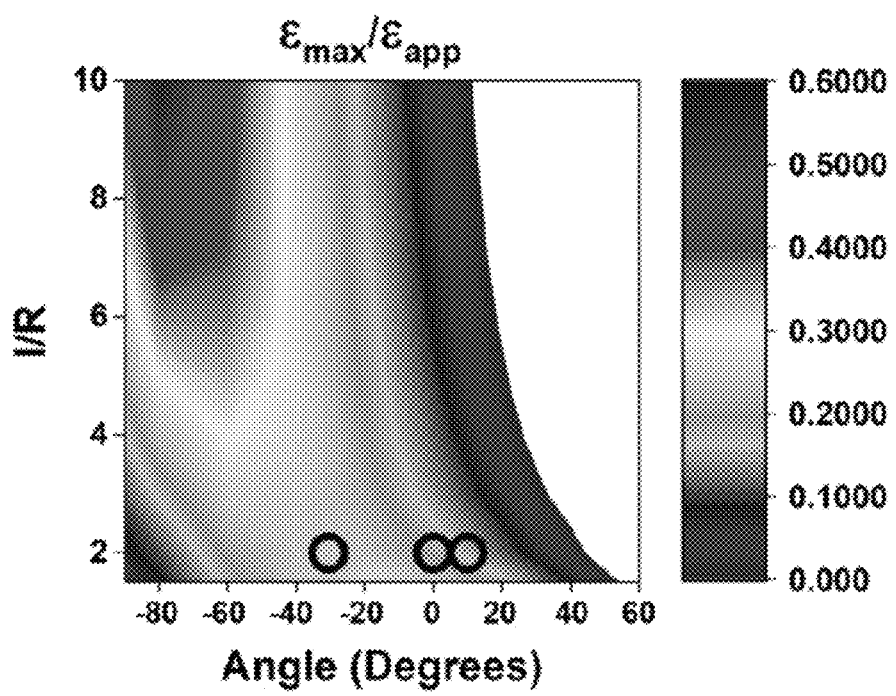
FIG. 3B: is an example according to various embodiments illustrating a contour plot of the maximum effective strain on the inner U-bend of a microserpentine, calculated from the analytical model developed using Equation 2, in which the lower values indicate a higher maximum effective strain that can be applied before failure, and in which circles indicate design choices according to various examples.

FIG. 3A is an example according to various embodiments illustrating a contour plot of the normalized stiffness for a microserpentine (with FORMLABS® Clear resin) calculated from the analytical model developed using Equation 1, in which the hotter colors denote conformation closer to the stiffness of a flat ribbon (where α=−90°), and in which circles indicate the design choices according to various examples. FIG. 3B is an example according to various embodiments illustrating a contour plot of the maximum effective strain on the inner U-bend of a microserpentine, calculated from the analytical model developed using Equation 2, in which the lower values indicate a higher maximum effective strain that can be applied before failure, and in which circles indicate design choices according to various examples.

FIGS. 3A and 3B, show contour plots of Equations 1 and 2. These contour plots represent the variation of normalized stiffness and $\varepsilon_{max}/\varepsilon_{applied}$, where the angle α was varied along the x-axis, and the ratio of l/R varied on the y-axis. In both the graphs, the quantity w/R was fixed for calculations because the width of the microserpentine never changed due to the experimental constraint previously mentioned. FIG. 3A was normalized with respect to the calculated values of the expected stiffness (Equation 1) for an α of −90°, where the microserpentine would devolve into a flat ribbon and thus would be the stiffest conformation. FIG. 3B, is a similarly derived contour plot representing analytical calculations from Equation 2, which denotes the maximum effective strain that would be applied to the inner curvature of the U-bends. The values denoted in white in FIGS. 3A and 3B, violate the "non-overlapping constraint," which represent designs that are mathematically and geometrically impossible. Printing at the smallest resolvable design conformation on a μSLA 3D printer has associated design challenges which limit combinations of l/R and a that were chosen in this work. The region in FIG. 3A corresponding to a normalized stiffness between 0-0.25, represents the design conformations of a possible microserpentine which would be the least stiff. While this might appear advantageous, theoretical and μSLA print constraints (including more scaffolding supports for longer "l" values), necessitate design choices that balance stiffness and effective strain.

Figure 4A:
FIG. 4A: is an example according to various embodiments illustrating a schematic representations of a microserpentine design in which $\alpha=-33°$.
Figure 4B:
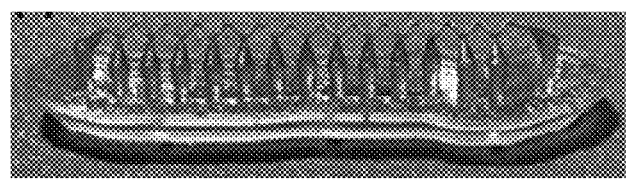
FIG. 4B: is an example according to various embodiments illustrating an optical image of a µSLA 3D printed microserpentines after metallization corresponding to the microserpentine design of FIG. 4A.
Figure 4C:
FIG. 4C: is an example according to various embodiments illustrating a schematic representations of a microserpentine design in which $\alpha=0°$.
Figure 4D:
FIG. 4D: is an example according to various embodiments illustrating an optical image of a µSLA 3D printed microserpentines after metallization corresponding to the microserpentine design of FIG. 4C.
Figure 4E:
FIG. 4E: is an example according to various embodiments illustrating a schematic representations of a microserpentine design in which $\alpha=10°$.
Figure 4F:
FIG. 4F: is an example according to various embodiments illustrating an optical image of a µSLA 3D printed microserpentines after metallization corresponding to the microserpentine design of FIG. 4E.

Three designs were chosen and are denoted on the graph with black circles in FIGS. 3A and 3B. All three of the variants had l/R ratios of 2 (with l=800 μm) in order to ensure non-overlapping print configurations, as higher values of "l" would have resulted in fused microserpentines at α=10°. As previously mentioned, there is a mutually exclusive relationship between the supporting scaffolds necessary to resolve microserpentines, and microserpentines with a lower stiffness value. A minimum of one linear support per "S" unit along the x-axis (denoted in FIG. 1B) is necessary to resolve the l/R=2 designs. Increasing the "l" value would increase scaffolding necessary for a "S" unit along the y-axis, to values >1. This would result in either fused prints, or unstable printed structures, negating benefits that are theoretically possible. This limitation narrowed down the real variation in design stretchability and flexibility to the value of α, which in fact does contribute greatly to the overall performance of a design. Values for α at 0° and 10° were chosen to illustrate (according to the calculated theoretical data), that the small increase of 10° would significantly have a positive impact the design (supported in FIG. 3B). The α=−33° was arbitrarily chosen in the negative region, to be closer to the mid-range of stiffness values, and to study negative design values of a. These decisions are supported by the analytical model for maximum strain that shows that the these values for the inner U-bends are inversely related to the overall maximum stretchability of the microserpentine design. FIGS. 4A, 4C, and 4E demonstrate the 3D CAD renderings of the three chosen microserpentine designs, and FIGS. 4B, 4D, and 4F illustrate the corresponding optical micrographs of the 3D printed and metallized designs before release from their printing support structures. FIG. 4A is an example according to various embodiments illustrating a schematic representations of a microserpentine design in which α=−33°. FIG. 4B is an example according to various embodiments illustrating an optical image of a μSLA 3D printed microserpentines after metallization corresponding to the microserpentine design of FIG. 4A. FIG. 4C is an example according to various embodiments illustrating a schematic representations of a microserpentine design in which α=0°. FIG. 4D is an example according to various embodiments illustrating an optical image of a μSLA 3D printed microserpentines after metallization corresponding to the microserpentine design of FIG. 4C. FIG. 4E is an example according to various embodiments illustrating a schematic representations of a microserpentine design in which α=10°. FIG. 4F is an example according to various embodiments illustrating an optical image of a μSLA 3D printed microserpentines after metallization corresponding to the microserpentine design of FIG. 4E.

Figure 5:
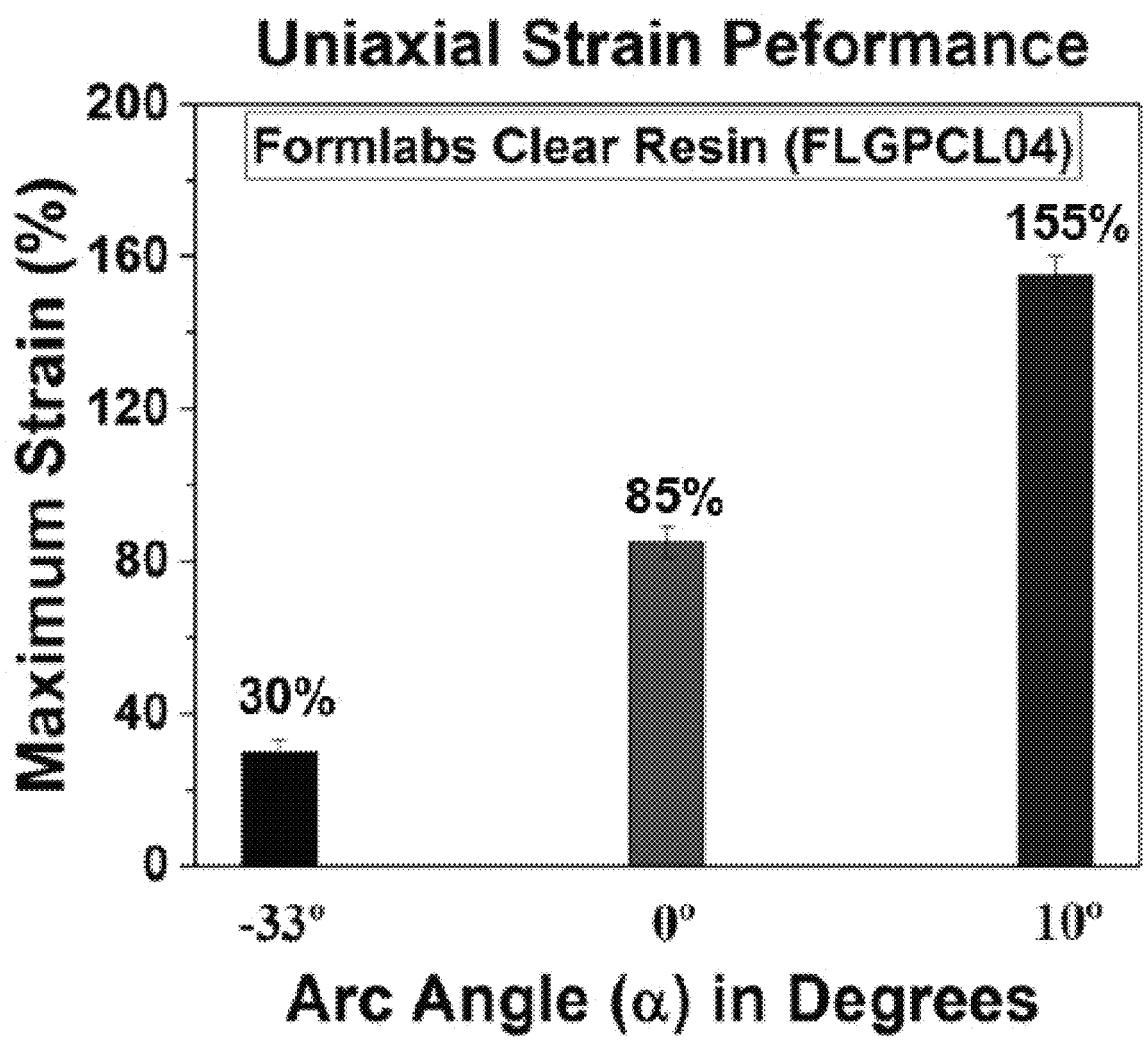
FIG. 5: is an example according to various embodiments illustrating a chart showing experimentally measured maximum uniaxial strain of the three microserpentine designs shown in FIGS. 4A-F, leading to the down selection of the $\alpha=10°$ design.

FIG. 5 is an example according to various embodiments illustrating a chart showing experimentally measured maximum uniaxial strain of the three microserpentine designs shown in FIGS. 4A-F, leading to the down selection of the α=10° design. FIG. 5 plots the effective maximum strain attained by the three designs experimentally (average N=6). The α=−33° design had the poorest performance with failure at 30% increase in length during uniaxial strain testing. The α=0° design performed largely better as expected, with the ability to extend up to a maximum of 85% additional strain from rest prior to failure.

Figure 6A:
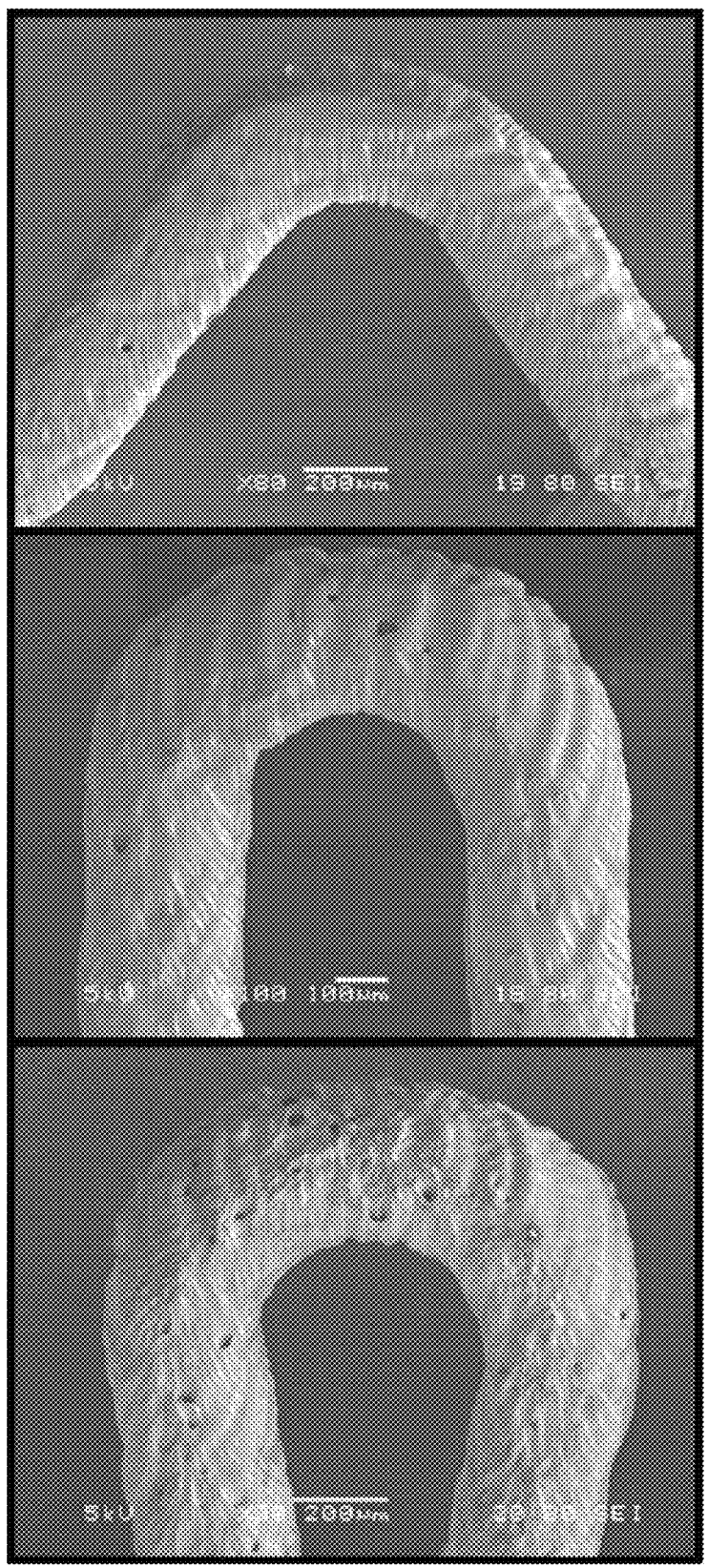
FIG. 6A: is an example according to various embodiments illustrating an SEM image of the microserpentine design corresponding to FIG. 4A and FIG. 4B, showing minor print defects from the μSLA printing process that do not impact the designs performance and are consistent across all prints.
Figure 6B:
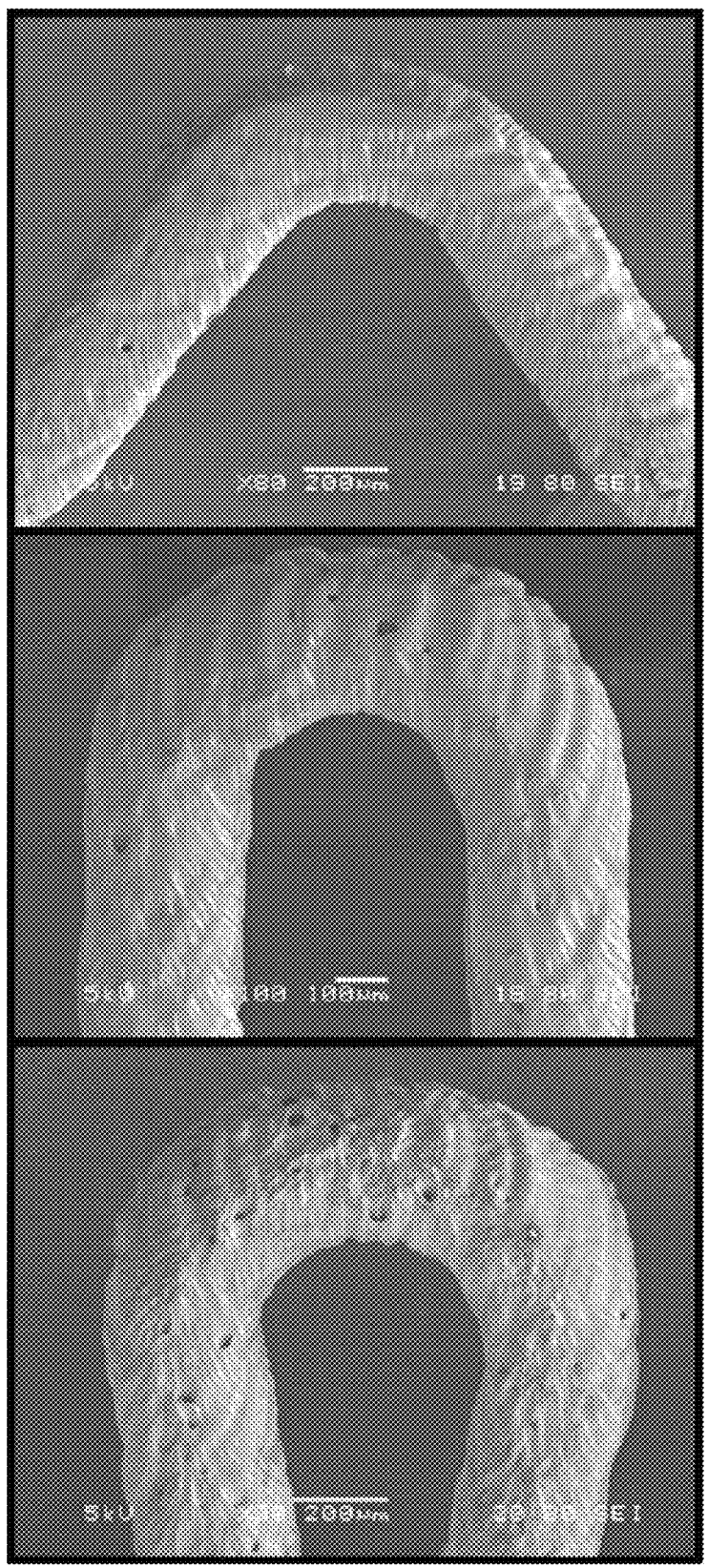
FIG. 6B: is an example according to various embodiments illustrating an SEM image of the microserpentine design corresponding to 4C and FIG. 4D, showing minor print defects from the μSLA printing process that do not impact the designs performance and are consistent across all prints.
Figure 6C:
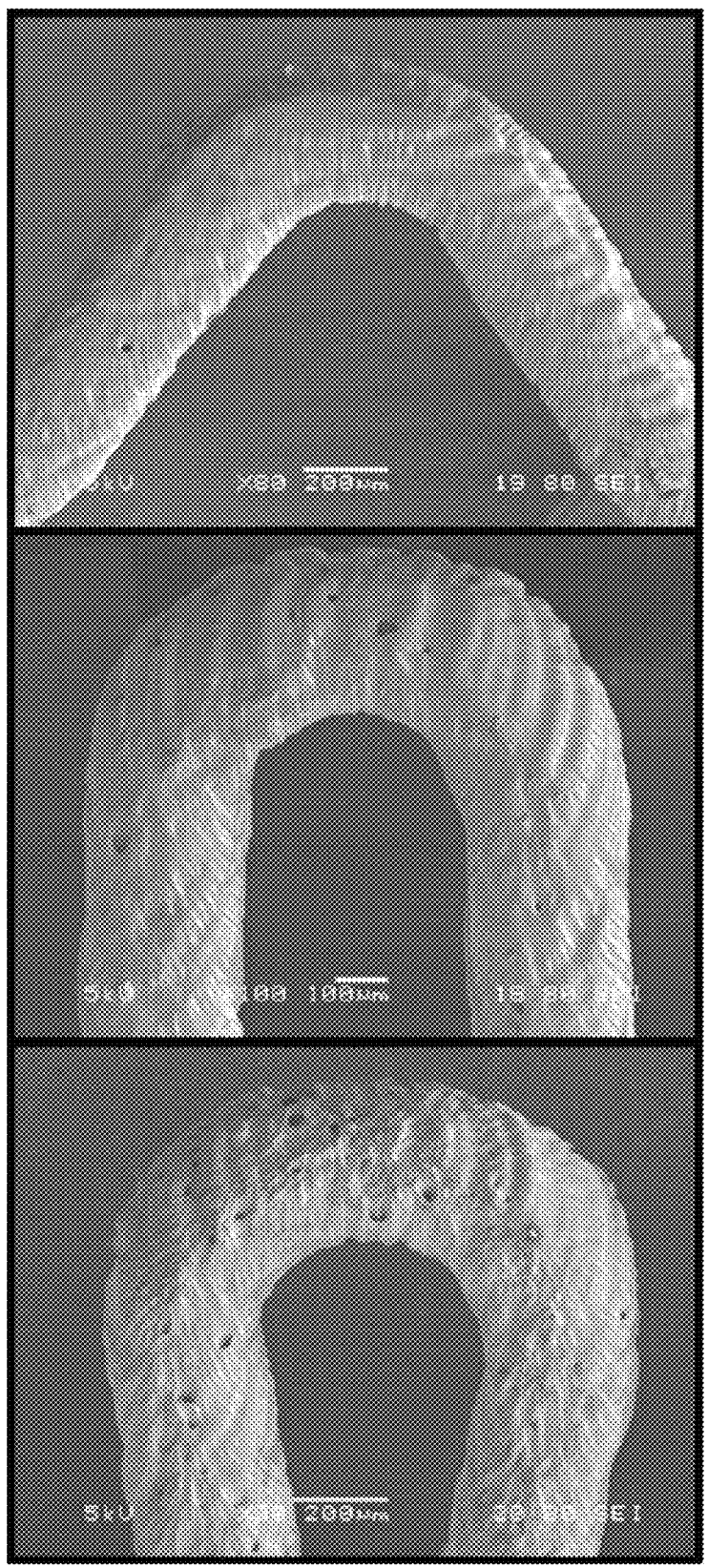
FIG. 6C: is an example according to various embodiments illustrating an SEM image of the microserpentine design corresponding to FIG. 4E and FIG. 4F, showing minor print defects from the μSLA printing process that do not impact the designs performance and are consistent across all prints.

FIG. 6A is an example according to various embodiments illustrating an SEM image of the microserpentine design corresponding to FIG. 4A and FIG. 4B, showing minor print defects from the μSLA printing process that do not impact the designs performance and are consistent across all prints. FIG. 6B is an example according to various embodiments illustrating an SEM image of the microserpentine design corresponding to 4C and FIG. 4D, showing minor print defects from the μSLA printing process that do not impact the designs performance and are consistent across all prints. FIG. 6C is an example according to various embodiments illustrating an SEM image of the microserpentine design corresponding to FIG. 4E and FIG. 4F, showing minor print defects from the μSLA printing process that do not impact the designs performance and are consistent across all prints. The optimized design (α=10° as suggested by the analytical model and expected to outperform the other two designs, was able to resist failure until a uniaxial strain of 155% was applied to the structure. This structure was chosen for further metallization optimization and device fabrication. FIGS. 6A, 6B, and 6C show SEM images of the three designs, after printing. The striations and small defects in the resin surface are standard features of μSLA printing, by virtue of the laser-spot definition of individual printed layers and did not have any significant impact on the performance of the microserpentine structures.

To accomplish conductive microserpentines toward the goal of 3D stretchable microelectrodes, a conformal metal deposition technique was needed that could coat the striated surface of the microserpentine and maintain its integrity under strain. Sputter metal coating provides an ideal, easily accessible method to accomplish conformal metal coatings with precisely defined thicknesses. Five different coating thicknesses (7 nm, 14 nm, 20 nm, 33 nm, and 70 nm) were assessed to obtain an optimal coating of sputtered gold, with resistance performance under strain as the measurand.

Figure 7A:
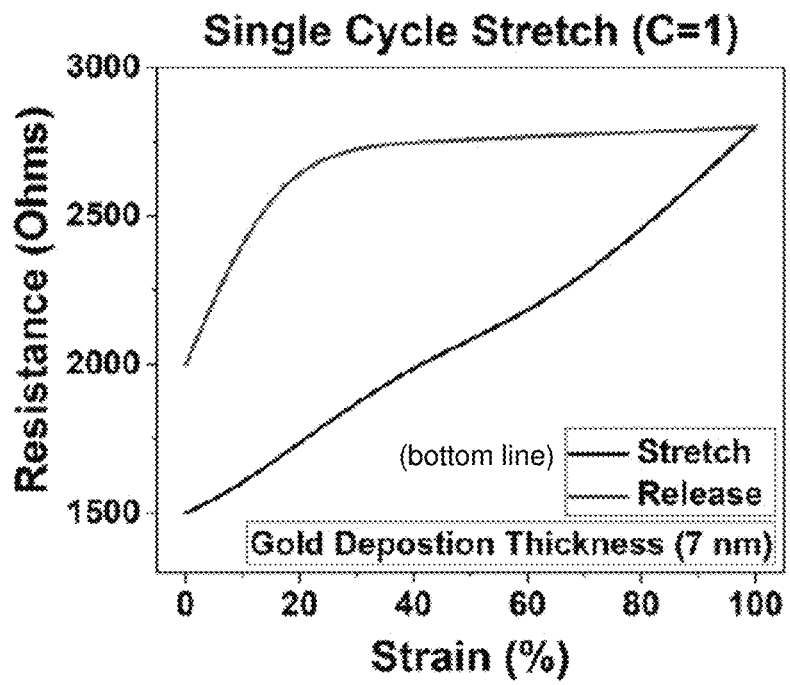
FIG. 7A: is an example according to various embodiments illustrating a single cycle hysteresis (strain and release) graph for a 7 nm Au coating.
Figure 7B:
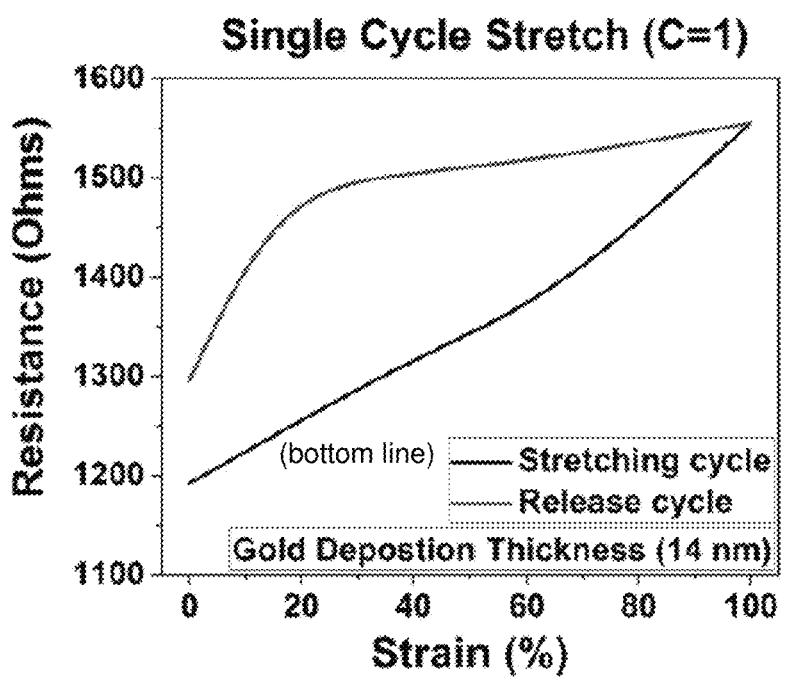
FIG. 7B: is an example according to various embodiments illustrating a single cycle hysteresis (strain and release) graph for a 14 nm coating.
Figure 7C:
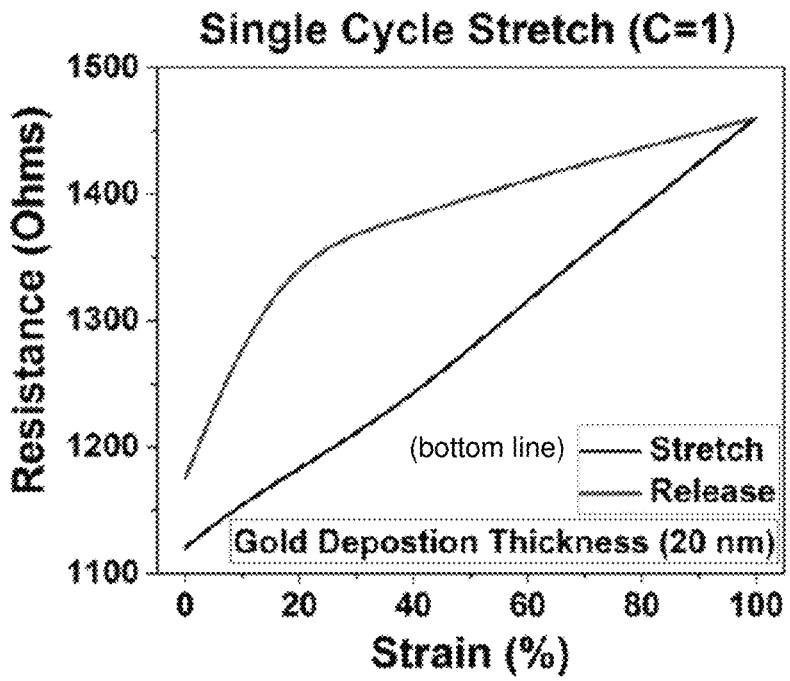
FIG. 7C: is an example according to various embodiments illustrating a single cycle hysteresis (strain and release) graph for a 20 nm coating.
Figure 7D:
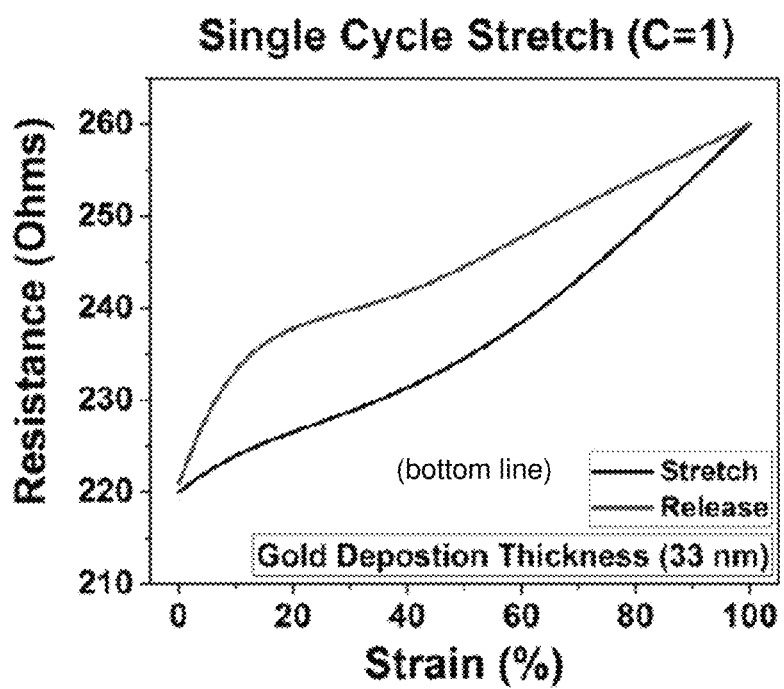
FIG. 7D: is an example according to various embodiments illustrating a single cycle hysteresis (strain and release) graph for a 33 nm coating.
Figure 7E:
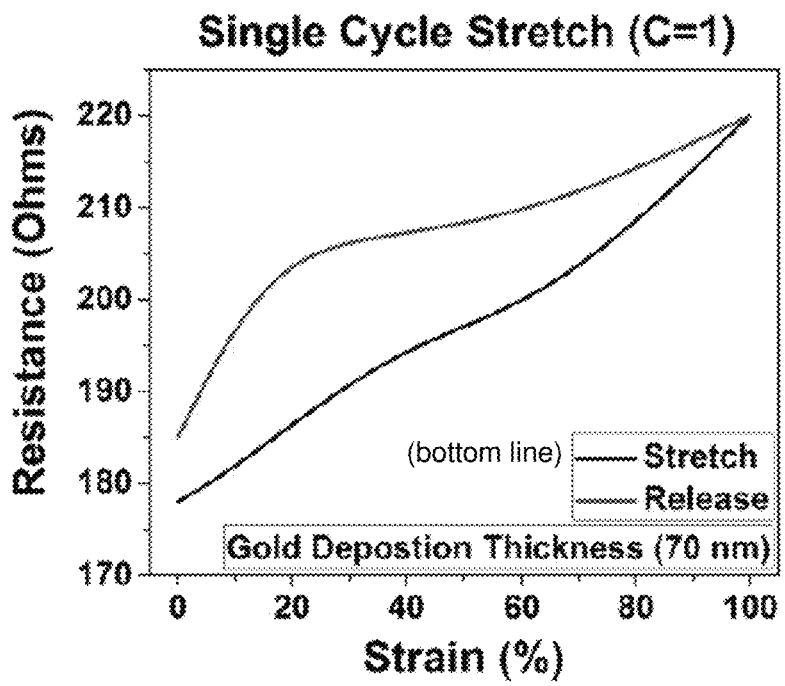
FIG. 7E: is an example according to various embodiments illustrating a single cycle hysteresis (strain and release) graph for a 70 nm coating.
Figure 7F:
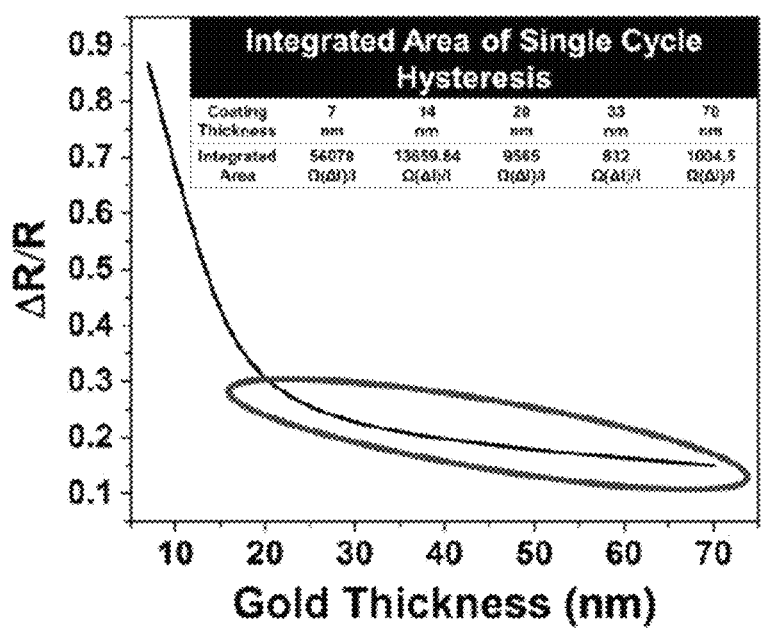
FIG. 7F: is an example according to various embodiments illustrating $\Delta R/R$ for each of the coating thicknesses of FIGS. 7A-E; in which the red highlighted area indicates coatings that are more suitable for consistent conduction performance over strain, including the 20 nm, 33 nm, and 70 nm coatings; and in which the inset table lists the tabulated hysteresis integration areas, indicating the most (33 nm) and least (7 nm) consistent conduction performance over the single cycle.

FIG. 7A is an example according to various embodiments illustrating a single cycle hysteresis (strain and release) graph for a 7 nm Au coating. FIG. 7B is an example according to various embodiments illustrating a single cycle hysteresis (strain and release) graph for a 14 nm coating. FIG. 7C is an example according to various embodiments illustrating a single cycle hysteresis (strain and release) graph for a 20 nm coating. FIG. 7D is an example according to various embodiments illustrating a single cycle hysteresis (strain and release) graph for a 33 nm coating. FIG. 7E is an example according to various embodiments illustrating a single cycle hysteresis (strain and release) graph for a 70 nm coating. FIG. 7F is an example according to various embodiments illustrating ΔR/R for each of the coating thicknesses of FIGS. 7A-E; in which the red highlighted area indicates coatings that are more suitable for consistent conduction performance over strain, including the 20 nm, 33 nm, and 70 nm coatings; and in which the inset table lists the tabulated hysteresis integration areas, indicating the most (33 nm) and least (7 nm) consistent conduction performance over the single cycle. FIGS. 7A, 7B, 7C, 7D, and 7E show the single cycle hysteresis for each of the five coating thicknesses, where the maximum strain value for the optimized α=10° design never exceeded 100% uniaxial strain (well below the maximum value of 155%, FIG. 5). The change in resistance to resistance at rest (ΔR/R) was calculated to see the reliability of each of the coatings during a single stretch cycle (FIGS. 7A, 7B, 7C, 7D, and 7E). FIG. 7F shows a plot of the ΔR/R values from the previous graphs (FIGS. 7A, 7B, 7C, 7D, and 7E), and highlights that asymptotic region encompassing the 20 nm, 33 nm, and 70 nm coatings. This low variance in the resistance values indicates that this asymptotic range is the most suitable for consistent conduction values while the device is under strain. This is evident when examining the requirements for viable microserpentine strain sensors, which require a much higher ΔR/R. The inset to FIG. 7F, corroborates this finding, as the integrated Ω(ΔI)/I, under the hysteresis curve are lowest for these three coatings as well: 7 nm corresponding to an integrated area of 56,070Ω(ΔI)/I, 14 nm with an area of 13,659.84Ω(ΔI)/I, 20 nm with an area of 9,565Ω(ΔI)/I, 33 nm with an area of 832Ω(ΔI)/I, and 70 nm with an area of 1,004.5Ω(ΔI)/I. This indicates a much tighter strain to relaxation behavior for the thicker coatings, which would improve device stability and reliability over time. The 33 nm has the lowest area under such a hysteresis curve and was chosen as the most reliable value for device construction.

To analyze fracture compositional changes in the coatings after the application of strain, Energy Dispersive X-Ray Spectroscopy (EDS) was performed on the coatings with the lowest area under such a hysteresis curve. FIG. 8A is an example according to various embodiments illustrating SEM and associated EDS data for analysis of an Au coating thickness of 20 nm after the application of uniaxial strain, in which circle 81 and circle 82 indicate points where EDS analysis was performed, with circle 81 being inside a fracture point, and circle 82 being outside a fracture point. FIG. 8B is an example according to various embodiments illustrating SEM and associated EDS data for analysis of an Au coating thickness of 33 nm after the application of uniaxial strain, in which circle 83 and circle 84 indicate points where EDS analysis was performed, with circle 83 being inside a fracture point, and circle 84 being outside a fracture point. FIG. 8C is an example according to various embodiments illustrating SEM and associated EDS data for analysis of an Au coating thickness of 70 nm after the application of uniaxial strain, in which circle 85 and circle 86 indicate points where EDS analysis was performed, with circle 85 being inside a fracture point, and circle 86 being outside a fracture point. FIG. 8D is an example according to various embodiments illustrating an SEM image of a separate 70 nm thick Au coating on a microserpentine after the application of strain, demonstrating much large fracturing of the Au film. FIGS. 8A, 8B, and 8C depicts SEM images of the (A) 20 nm, (B) 33 nm, and (C) 70 nm U-bends and the associated fractures in the gold film from applied strain, after being subjected to one-cycle strain and relaxation. Each SEM has two highlighted sections for compositional comparison using EDS: the red circle denotes regions inside the fracture, and blue circle denotes regions in the unaffected gold film outside the fracture. The focus of the fracture study was placed on the inner curvature of the U-bend as informed by the analytical model since these areas would be areas of the highest strain concentration. This observation was conformed during experimental analysis of the structures after strain application under the SEM. The SEM images show fracture occurring in all three coating thicknesses under strain. However, upon releasing the strain it was expected that the coatings would behave differently, and it was hypothesized that the fracture composition of the 33 nm coating would provide clues to its behavior.

Figures 9A, 9B, 9C, 9D, 9E, 9F:
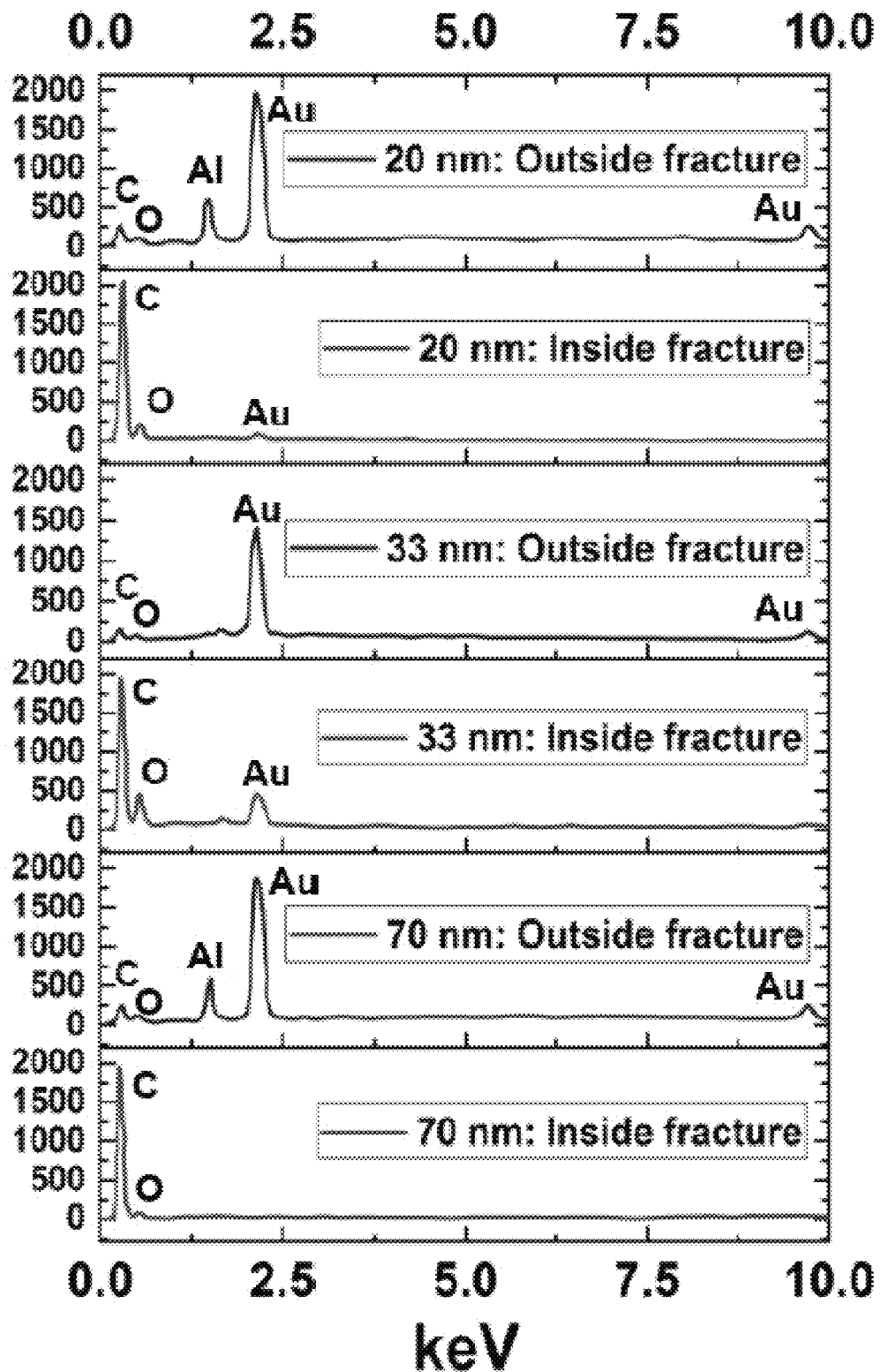
FIG. 9A: is an example according to various embodiments illustrating EDS data at circle 82 as shown in FIG. 8A.
FIG. 9B: is an example according to various embodiments illustrating EDS data at circle 81 as shown in FIG. 8A.
FIG. 9C: is an example according to various embodiments illustrating EDS data at circle 84 as shown in FIG. 8B.
FIG. 9D: is an example according to various embodiments illustrating EDS data at circle 83 as shown in FIG. 8B.
FIG. 9E: is an example according to various embodiments illustrating EDS data at circle 86 as shown in FIG. 8C.
FIG. 9F: is an example according to various embodiments illustrating EDS data at circle 85 as shown in FIG. 8C.

FIG. 9A is an example according to various embodiments illustrating EDS data at circle 82 as shown in FIG. 8A. FIG. 9B is an example according to various embodiments illustrating EDS data at circle 81 as shown in FIG. 8A. FIG. 9C is an example according to various embodiments illustrating EDS data at circle 84 as shown in FIG. 8B. FIG. 9D is an example according to various embodiments illustrating EDS data at circle 83 as shown in FIG. 8B. FIG. 9E is an example according to various embodiments illustrating EDS data at circle 86 as shown in FIG. 8C. FIG. 9F is an example according to various embodiments illustrating EDS data at circle 85 as shown in FIG. 8C. With respect to FIGS. 9A-9F, it was generally observed that more Au was located outside of the fracture, as was expected, and the main difference in the analysis was the amount of Au that remained in the fracture. FIGS. 9A, 9B, 9C, 9D, 9E, and 9F show the EDS data from the performed experiment. It is observed that all three coating thicknesses, gold is abundantly present outside the fracture point under strain. The significant differences occur when the EDS is performed inside the micro-fracture areas. While peaks for oxygen and carbon (denoting the resin underneath the gold) are observed in all three coatings, only the 33 nm thickness shows a significant amount of gold inside the micro-fracture region, relative to the other two coatings. This could explain the lower area under such a hysteresis curve for this coating. The aluminum peak in the EDS data is attributed to the background metal spectrum of the sample stage. FIG. 8D is an SEM image, illustrating the sharp micro-fracture occurring in the 70 nm coating, which could explain the increased resistance observed once at the end of the strain application cycle in FIGS. 7A-E.

Figure 10A:
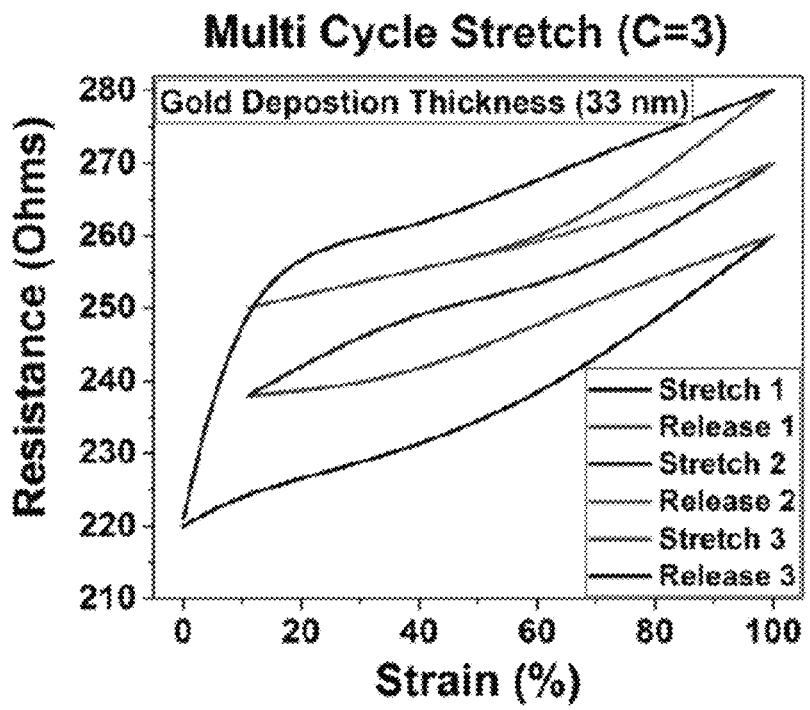
FIG. 10A: is an example according to various embodiments illustrating results of a multicycle hysteresis analysis of the 33 nm Au coatings on the microserpentine.
Figure 10B:
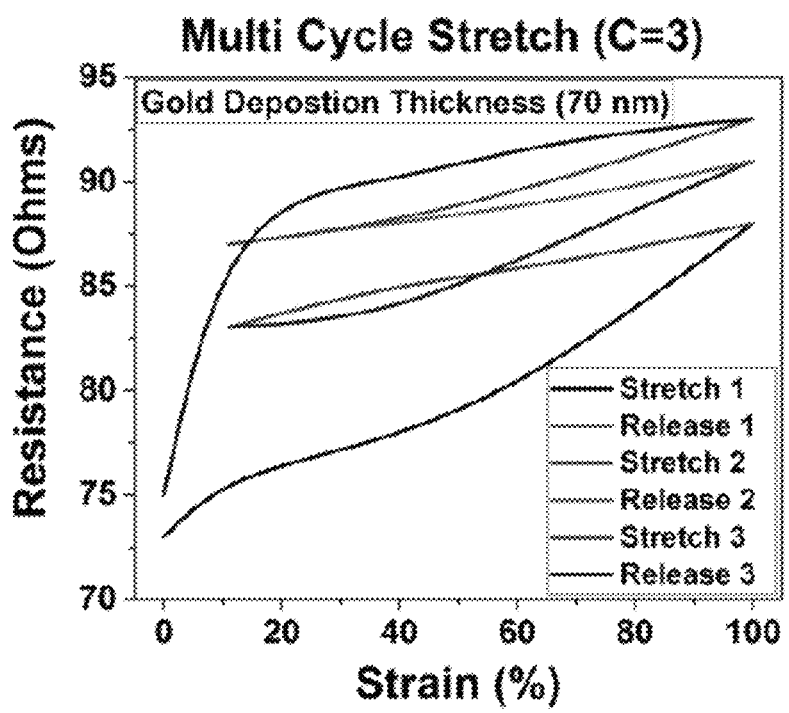
FIG. 10B: is an example according to various embodiments illustrating results of a multicycle hysteresis analysis of the 70 nm Au coatings on the microserpentine.
Figure 10C:
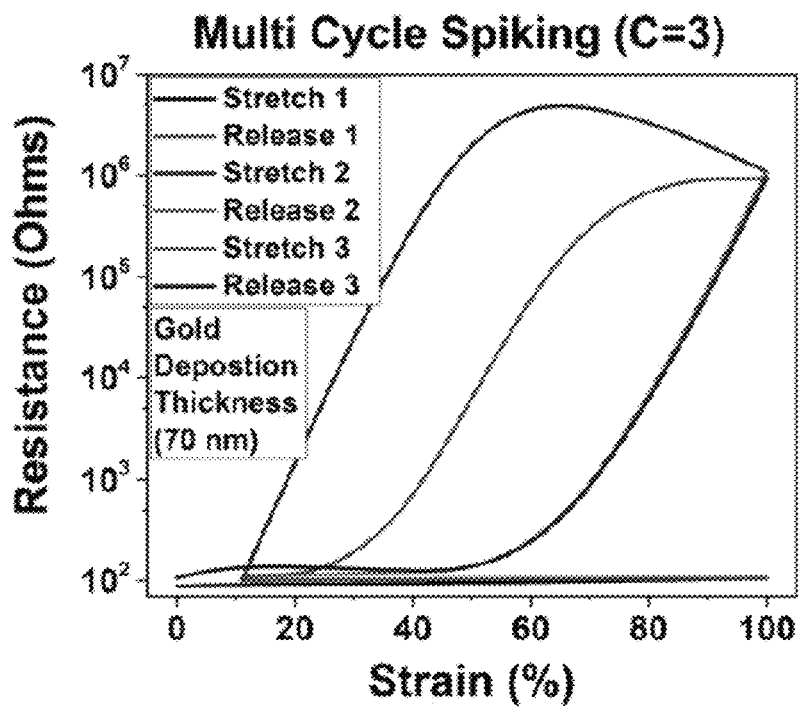
FIG. 10C: is an example according to various embodiments illustrating results of a multicycle hysteresis analysis of the coating shown in FIG. 8D on the microserpentine, and indicating the larger film fracturing samples from FIG. 8D demonstrate a large strain spiking signature.
Figure 10D:
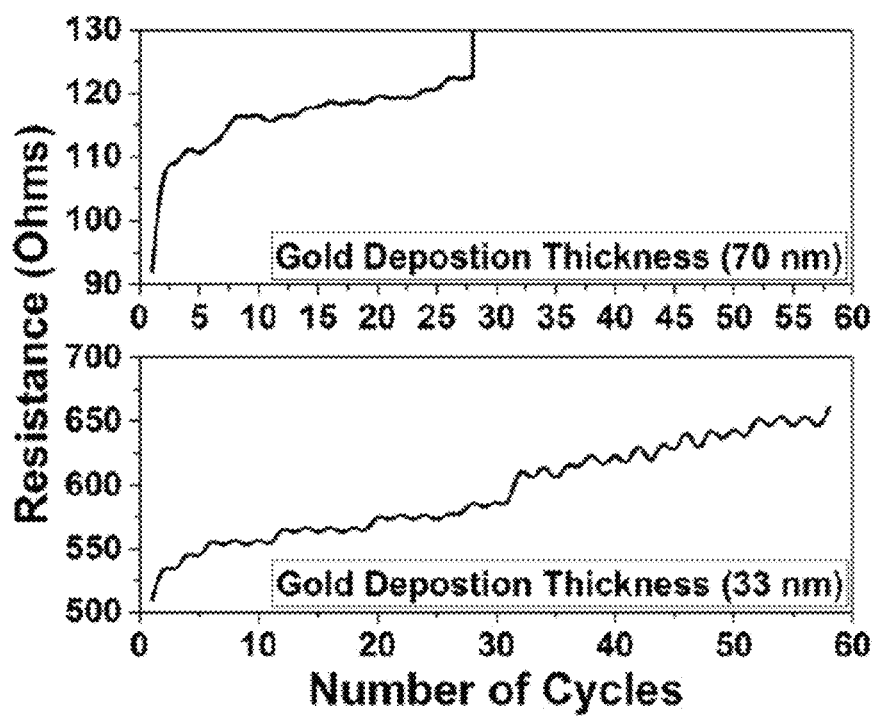
FIG. 10D: is an example according to various embodiments illustrating Reliability measurements during fatigue testing for both the 33 nm and 70 nm Au coatings, further demonstrating the choice of 33 nm as an optimized coating thickness according to various embodiments.

In order to obtain fatigue limits of these coatings on the optimized microserpentines, repeated strains were applied to the 33 nm and 70 nm coated microserpentines. FIG. 10A is an example according to various embodiments illustrating results of a multicycle hysteresis analysis of the 33 nm Au coatings on the microserpentine. FIG. 10B is an example according to various embodiments illustrating results of a multicycle hysteresis analysis of the 70 nm Au coatings on the microserpentine. Comparing FIGS. 10A and 10B shows that the performance of both coatings is similar. FIG. 10C is an example according to various embodiments illustrating results of a multicycle hysteresis analysis of the coating shown in FIG. 8D on the microserpentine and indicating the larger film fracturing samples from FIG. 8D demonstrate a large strain spiking signature. FIG. 10D is an example according to various embodiments illustrating Reliability measurements during fatigue testing for both the 33 nm and 70 nm Au coatings, further demonstrating the choice of 33 nm as an optimized coating thickness according to various embodiments. FIGS. 10A and 10B show the strain and release profiles for the 33 nm and 70 nm coatings (C=3 cycles) respectively. These results are similar to a single cycle results observed in FIGS. 7A-E. The three-cycle hysteresis curve shown in FIG. 10C illustrates irregularities observed in the 70 nm coated microserpentines. More than half of the tests performed at this thickness contain seemingly random spiking activity during any of its strain cycles. As mentioned previously in the EDS data of FIGS. 9A-F and the associated SEM images of FIGS. 8C and 8D, the 70 nm coating separates dramatically during strain, which directly contributes to the spiking seen in these cycles. Fatigue limit of both the 33 nm and the 70 nm coating on the optimized $\alpha=10°$ microserpentine is depicted in FIG. 10D. The 70 nm coating is observed to fail in under 30 strain cycles, whereas the 33 nm coating continues to perform up to 60 cycles of strain indicating approximately double the fatigue limit. These observed results were the rationale to pursue the 33 nm coating, which demonstrated a more reliable performance.

Figure 11A:
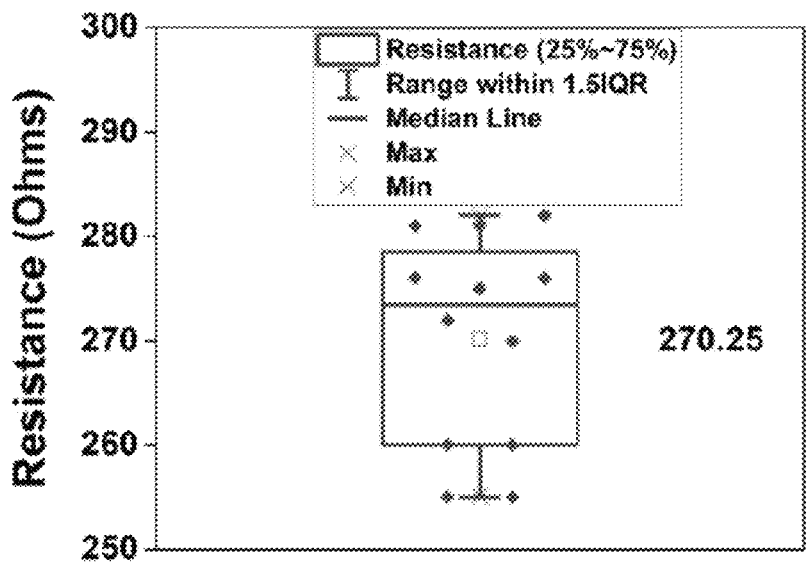
FIG. 11A: is an example according to various embodiments illustrating twisting conformation of the 33 nm Au coated microserpentine, demonstrating a tight resistance signature for N=11 twists.
Figure 11B:
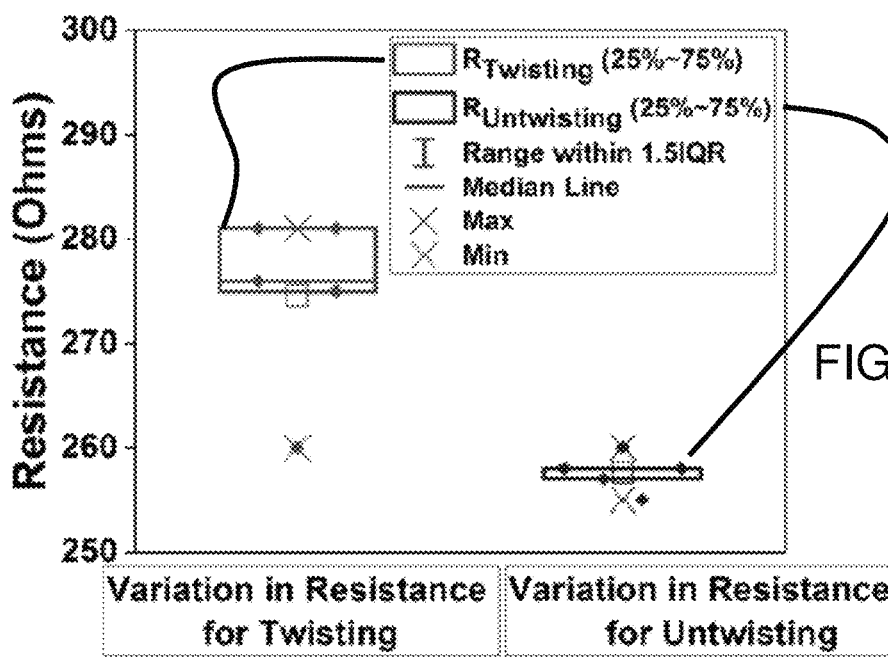
FIG. 11B: is an example according to various embodiments illustrating a twisting signature plot similar to that shown in FIG. 11A, but incorporating resistance values for N=5 twisting and untwisting cycles, also demonstrating a tight grouping.
Figure 11C:
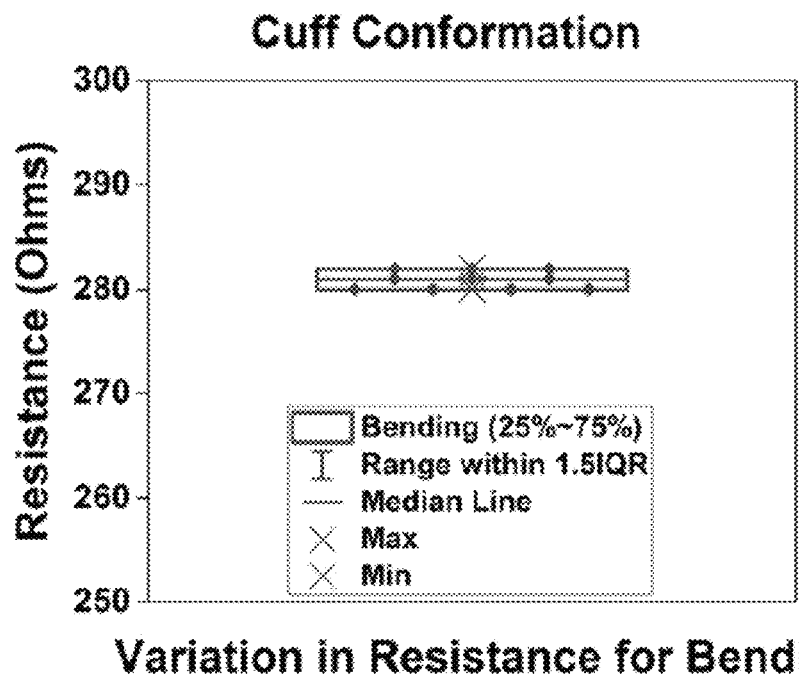
FIG. 11C: is an example according to various embodiments illustrating a cuff conformation resistance plot for the microserpentine, showing reliable performance after greater than N=25 bends.
Figure 11D:
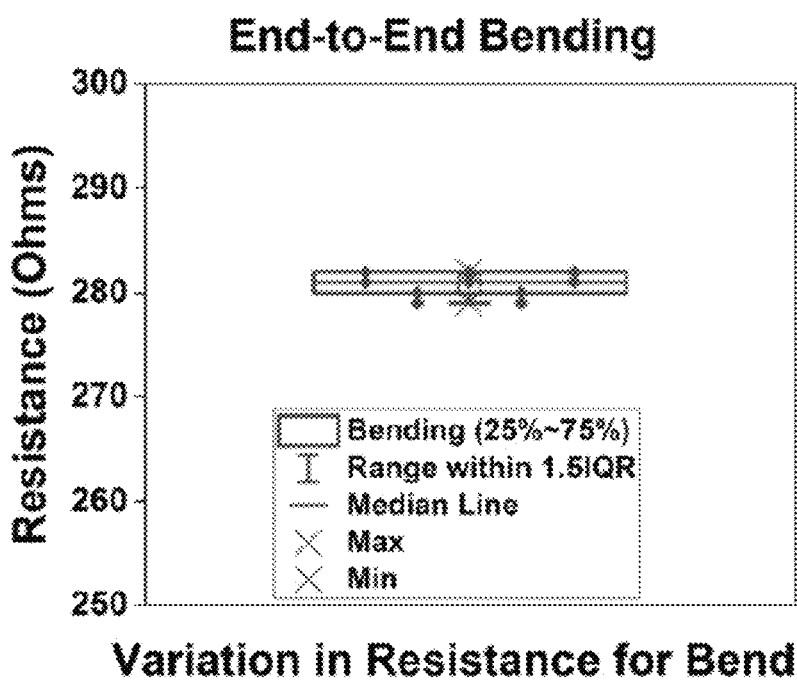
FIG. 11D: is an example according to various embodiments illustrating end-to-end bending of the microserpentine, also demonstrating a very similar tight grouping to FIG. 11C.

FIG. 11A is an example according to various embodiments illustrating twisting conformation of the 33 nm Au coated microserpentine, demonstrating a tight resistance signature for N=11 twists. FIG. 11B is an example according to various embodiments illustrating a twisting signature plot similar to that shown in FIG. 11A, but incorporating resistance values for N=5 twisting and untwisting cycles, also demonstrating a tight grouping. FIG. 11C is an example according to various embodiments illustrating a cuff conformation resistance plot for the microserpentine, showing reliable performance after greater than N=25 bends. FIG. 11D is an example according to various embodiments illustrating end-to-end bending of the microserpentine, also demonstrating a very similar tight grouping to FIG. 11C. FIGS. 11A, 6B, 6C, and 6D demonstrate the electrical characterization through resistance measurements, of the microserpentine base structure under twisting, bending and conformation. FIG. 11A shows the tight resistance distribution (mean of 275Ω); +/−10.0Ω) of the optimized microserpentine design as it is twisted for N=11 cycles prior to becoming unusable. FIG. 11B shows the slight variance of the resistance values (mean of 278Ω); +/−8.62Ω) during N=5 twist cycles, and the subsequent N=5 turns to untwist the microserpentine (mean of 260 Ω; +/−1.82Ω).

Figure 12A:
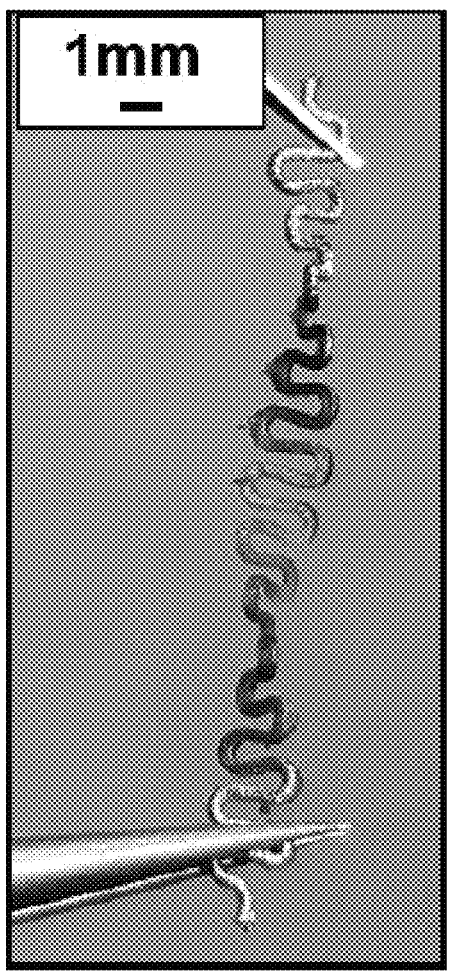
FIG. 12A: is an example according to various embodiments illustrating an optical image of twisting the microserpentine.
Figure 12B:
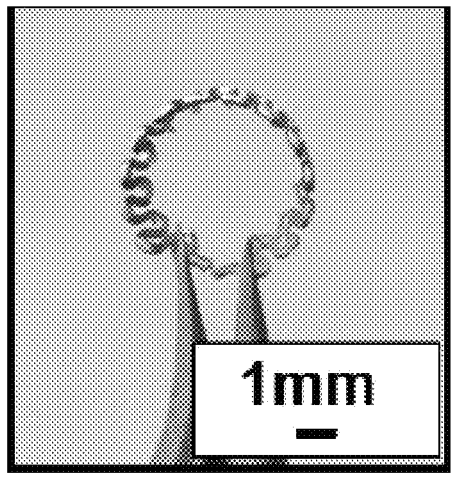
FIG. 12B: is an example according to various embodiments illustrating an optical image of the microserpentine in a cuff conformation.
Figure 12C:
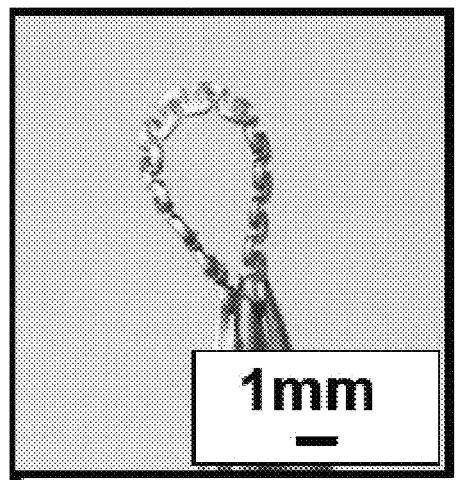
FIG. 12C: is an example according to various embodiments illustrating an optical image of the end-to-end bending of the microserpentine.

FIG. 12A is an example according to various embodiments illustrating an optical image of twisting the microserpentine. FIG. 12B is an example according to various embodiments illustrating an optical image of the microserpentine in a cuff conformation. FIG. 12C is an example according to various embodiments illustrating an optical image of the end-to-end bending of the microserpentine. The variance from higher twisting to untwisting values is attributable to the relaxation of the gold coating, and further demonstrates the reliability of the 33 nm coating. FIG. 11C shows the resistance values (mean of 282 Ω; +/−0.88Ω) for the cuff conformation of the microserpentine device, and FIG. 11D shows a very similar and tight grouping for the resistance values for an end-to-end bending conformation (mean of 282Ω); +/−1.16Ω). The images in FIGS. 12A, 12B, and 12C are micrographs of the twisting and bending conformations performed, with FIG. 12A representing data shown in FIGS. 11A and 11B; FIG. 12B representing data shown in FIG. 11C; and FIG. 12C representing data shown in FIG. 11D. The stability of the resistance in all these conformations further lends credence to microserpentine optimization for a microelectrode application.

Figure 13A:
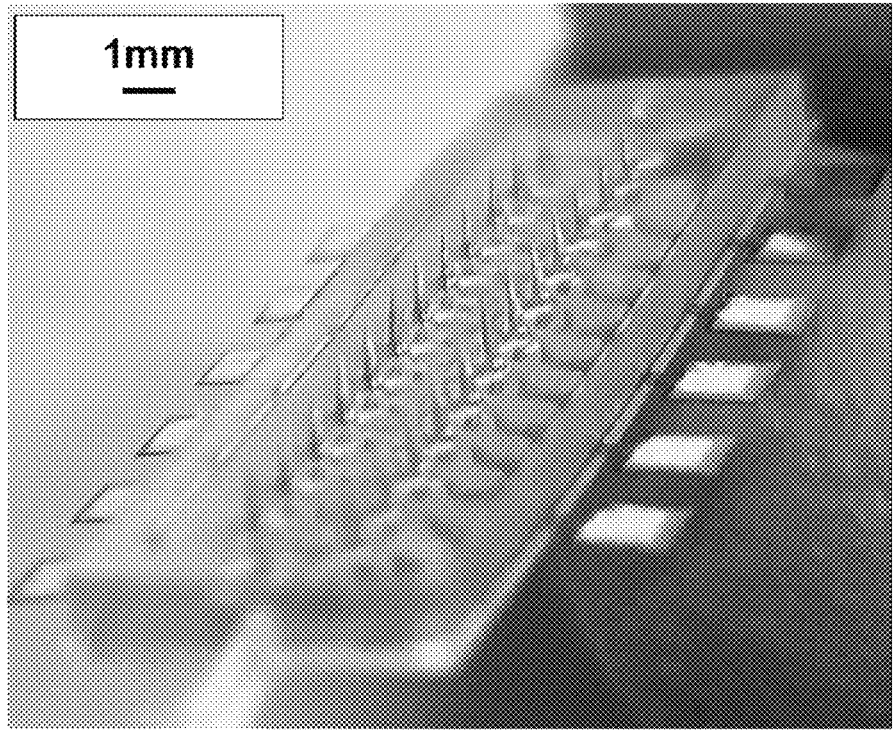
FIG. 13A: is an example according to various embodiments illustrating an optical image of the fully assembled 3D microelectrode device, schematically represented in FIG. 2D.
Figure 13B:
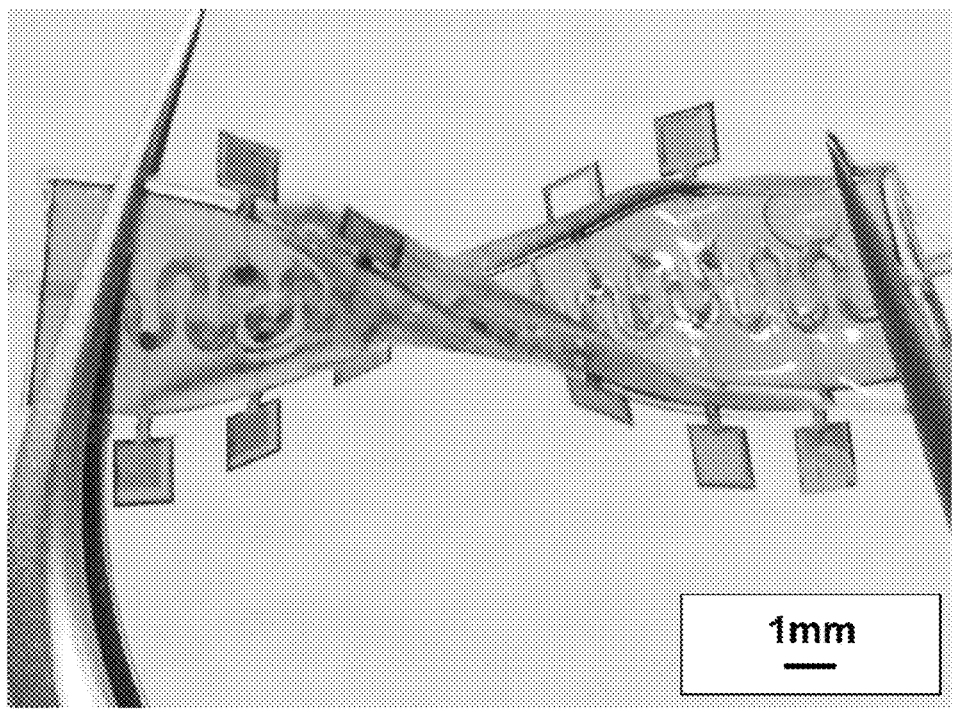
FIG. 13B: is an example according to various embodiments illustrating an optical image of the microelectrode microserpentine device shown in FIG. 13A undergoing twisting with a pair of tweezers.
Figure 13C:
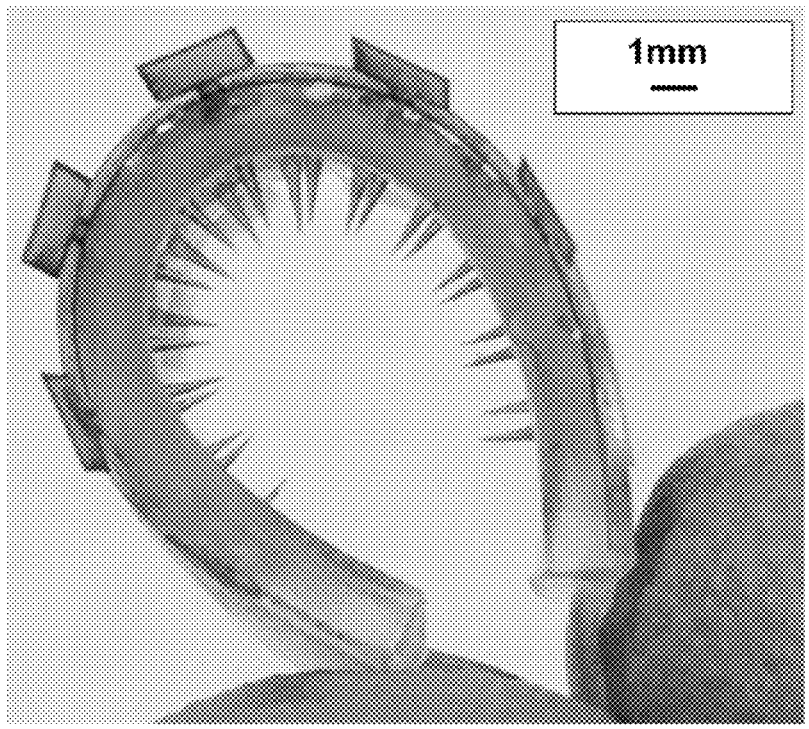
FIG. 13C: is an example according to various embodiments illustrating an optical image of the 3D microserpentine microelectrode device shown in FIGS. 13A and 13B undergoing end-to-end bending.
Figure 13D:
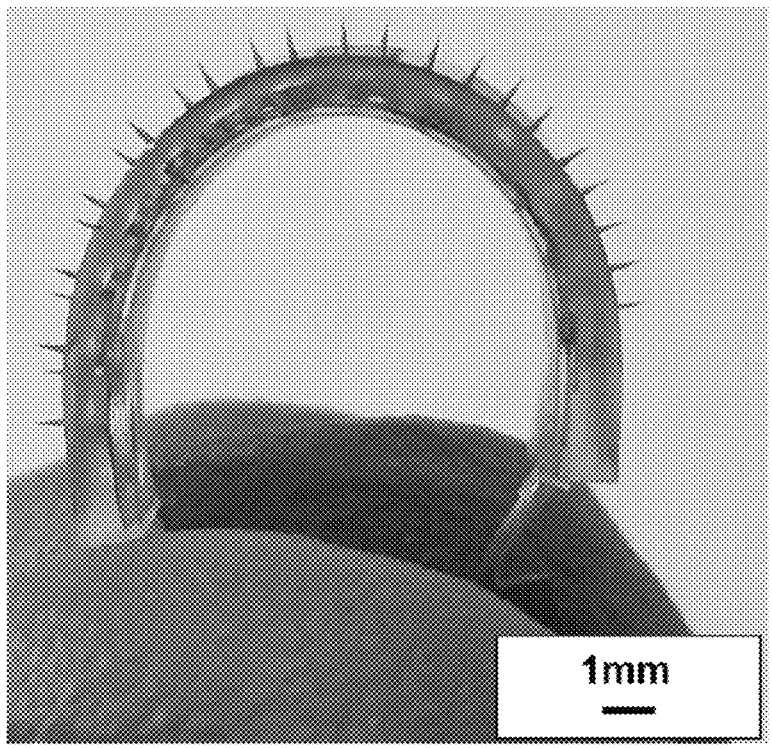
FIG. 13D: is an example according to various embodiments illustrating an optical image of the microelectrode microserpentine device shown in FIGS. 13A-C in a reverse cuff conformation, exposing the microelectrode needle tips for imaging.

FIG. 13A is an example according to various embodiments illustrating an optical image of the fully assembled 3D microelectrode device, schematically represented in FIG. 2D. FIG. 13B is an example according to various embodiments illustrating an optical image of the microelectrode microserpentine device shown in FIG. 13A undergoing twisting with a pair of tweezers. FIG. 13C is an example according to various embodiments illustrating an optical image of the 3D microserpentine microelectrode device shown in FIGS. 13A and 13B undergoing end-to-end bending. FIG. 13D is an example according to various embodiments illustrating an optical image of the microelectrode microserpentine device shown in FIGS. 13A-C in a reverse cuff conformation, exposing the microelectrode needle tips for imaging. FIGS. 13A, 13B, 13C, and 13D demonstrate the fully integrated and assembled 3D printed, microserpentine 3D microelectrodes for biosensor applications. FIG. 13A shows the design to device translation, representing a highly controllable and repeatable fabrication process. FIGS. 13B, 13C, and 13D depict the flexibility of this fully encapsulated device (KAPTON® package and PDMS insulation) in several key conformations. FIG. 13B shows a twisting configuration. FIG. 13C shows a cuff configuration. FIG. 13D shows an outward end-to-end bending configuration. The device was robust enough to recover its original shape immediately, after the application of these flexural strains. The fabrication can be adapted potentially with a PDMS package and liquid EInGaN or cPDMS metallic traces to achieve a fully stretchable biosensor. As an initial step in device demonstration, KAPTON® was chosen due to its thermal stability, ease of defining through laser-micromachining, and good adhesion properties to deposited metal traces. Polydimethylsiloxane (PDMS) has been experimentally observed, to be inhibited from curing at the interface between the resin and the elastomer. However, through the metallization of the 3D printed microserpentine (a necessary step in the device microfabrication), no issues with curing the PDMS layer on the 3D printed resin were observed.

FIG. 14A is an example according to various embodiments illustrating an SEM image of the fully assembled device, in which the highlighted regions denote where the laser isolation trace is located beneath the PDMS layer (and hence are difficult to visualize), and where the exposed circular electrode tips emerge from the PDMS layer. FIG. 14B is an example according to various embodiments illustrating an SEM image of the exposed electrode tip, in which, after insulation, it is estimated that the electrode tips are 300 µm in height above the surface of the PDMS. FIG. 14C is an example according to various embodiments illustrating an SEM close-up of the electrode tip from FIG. 14B, highlighting the naturally formed µSLA striations which contribute to the increased effective surface area of the 3D microelectrode. FIG. 14A shows an SEM overview of the fully encapsulated and fabricated microelectrode device. The uninsulated electrode tips can be observed emerging from the PDMS, while the underlying microserpentine structure can also be observed due to the conformal nature of PDMS coating and casting. The laser micromachined scribe line to isolate the electrodes from one another can similarly be observed. FIG. 14B depicts a close-up SEM of the 3D printed, metallized electrode tips that are exposed above the PDMS insulation. Edge of this tip is shown in FIG. 14C, and the striations of the surface of the exposed tip can be viewed. The striations are formed in this way, due to the optimal µSLA printing conditions, in which a 45° print angle was determined to be ideal for resolving the full electrode towers.

Figure 15A:
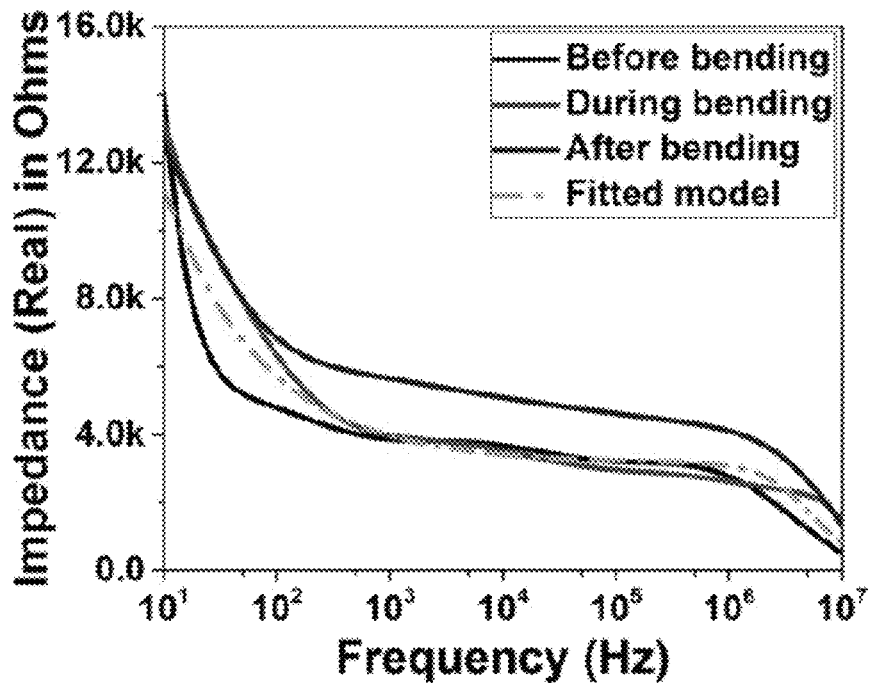
FIG. 15A: is an example according to various embodiments illustrating a full spectrum impedance plot of the device before (black), during (red) and after (blue) bending, with a fitted impedance model (green) from which relevant circuit parameters were extracted.
Figure 15B:
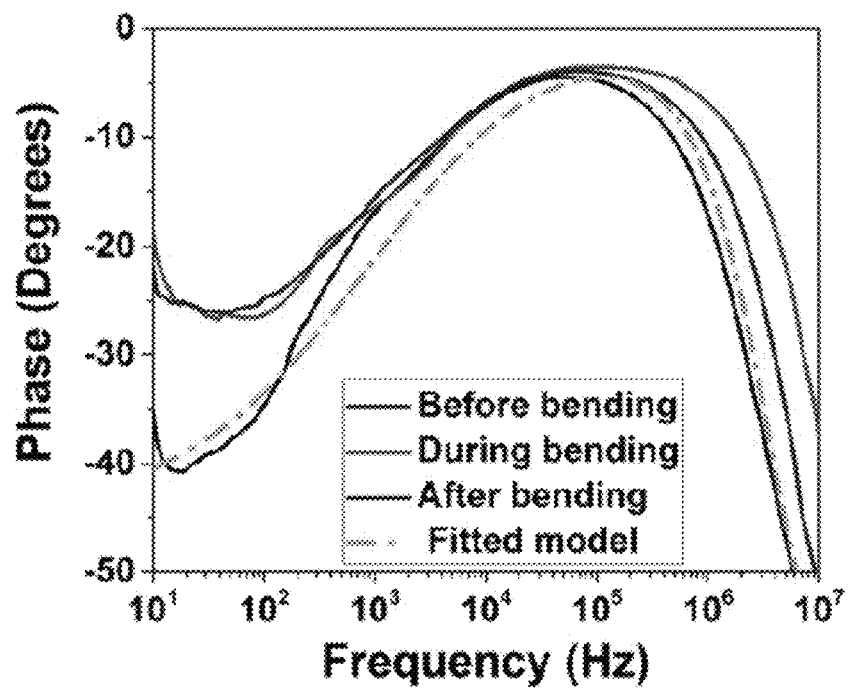
FIG. 15B: is an example according to various embodiments illustrating a full spectrum phase graph for the device before (black), during (red) and after (blue) bending, with a fitted impedance model (green) from which relevant circuit parameters were extracted.
Figures 15C, 15D:
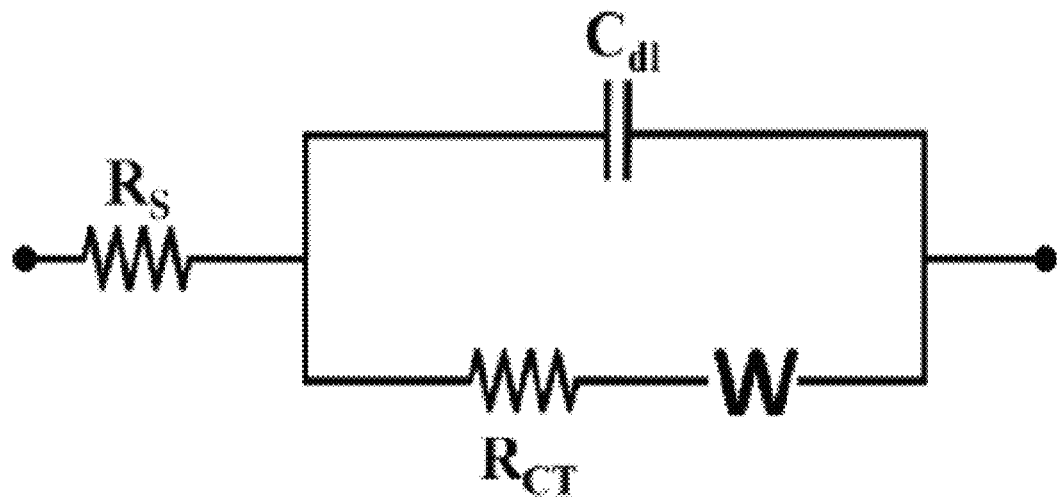
FIG. 15C: is an example according to various embodiments illustrating a representative circuit model for the microelectrode array profile extracted from FIGS. 15A and 15B.
FIG. 15D: is an example according to various embodiments illustrating extracted circuit parameters from the modeled circuit illustrated in FIG. 15C.

FIG. 15A is an example according to various embodiments illustrating a full spectrum impedance plot of the device before (black), during (red) and after (blue) bending, with a fitted impedance model (green) from which relevant circuit parameters were extracted. FIG. 15B is an example according to various embodiments illustrating a full spectrum phase graph for the device before (black), during (red) and after (blue) bending, with a fitted impedance model (green) from which relevant circuit parameters were extracted. FIG. 15C is an example according to various embodiments illustrating a representative circuit model for the microelectrode array profile extracted from FIGS. 15A and 15B. FIG. 15D is an example according to various embodiments illustrating extracted circuit parameters from the modeled circuit illustrated in FIG. 15C. FIGS. 15A, 15B, 15C, and 15D compiles the electrical characterization of the 3D microelectrode microserpentine device. FIG. 15A shows the full spectrum (10 Hz to 10 MHz) impedance of the electrode tips (~300 µm in height) before, during, and after bending strain was applied to the devices. At the electrophysiologically relevant frequency of 1 kHz, the real part of the complex impedance was measured to be 4.2 kΩ (before), 4.6 kΩ (during), and 5.2 kΩ (after) respectively (N=3). 3D printing high aspect ratio structures using µSLA processes, exaggerates the striations which are visible in FIG. 14C. Without wishing to be bound by theory, it is predicted that the higher surface area created by these striations, lowered the impedance values measured.

Typically to this end, nanomaterial electro- or electroless-plating has been one highly used method for increasing the surface area of microelectrodes, in order to help better extract biologically relevant data. The micro-texturing inherent in 3D printing could aid in impedance reduction for these interfaces. FIG. 15B represents phase values of full spectrum impedance before, during and after the application of bending strain. The phase spectra depict characteristically microelectrode profiles, starting as capacitive at phase between −20° and −40°, and gradually becoming more resistive as the frequency increases, and the phase value approaches 0°. The phase data suggests a pattern observed by us and other microelectrode researchers, in which the electrical profile of the mid-range frequencies is governed by a double layer capacitance ($C_{DL}$). The electrode-electrolyte interfacial impedance which occurs, is dominated by the resistive elements of the Phosphate Buffer Solution (PBS) solution at higher frequencies, and as a result slightly more negative phase values are observed. An analytical microelectrode model is fitted to the real and phase parts of the impedance based on the circuit schematic shown in FIG. 15C, which represents the components of a complete MEA: solution resistance ($R_S$), charge transfer resistance ($R_{CT}$), double layer capacitance ($C_{DL}$), and the Warburg element (W).

For extraction of the circuit parameters listed, Equation 3 is solved:

$$Z(\omega)=R_S+[1/(C_{dl}(\omega)+\{1/(R_{CT}+W(\omega))\}] \qquad (3)$$

The analytical model fits the experimental data well, demonstrating the impact of the components on the final electrical profile of the sputter coated, 3D microserpentine gold microelectrode. FIG. 15D contains a table of the extracted values of the equivalent circuit, for the analytical model that represents the combined three device states (before, during, and after bending).

Figure 16A:
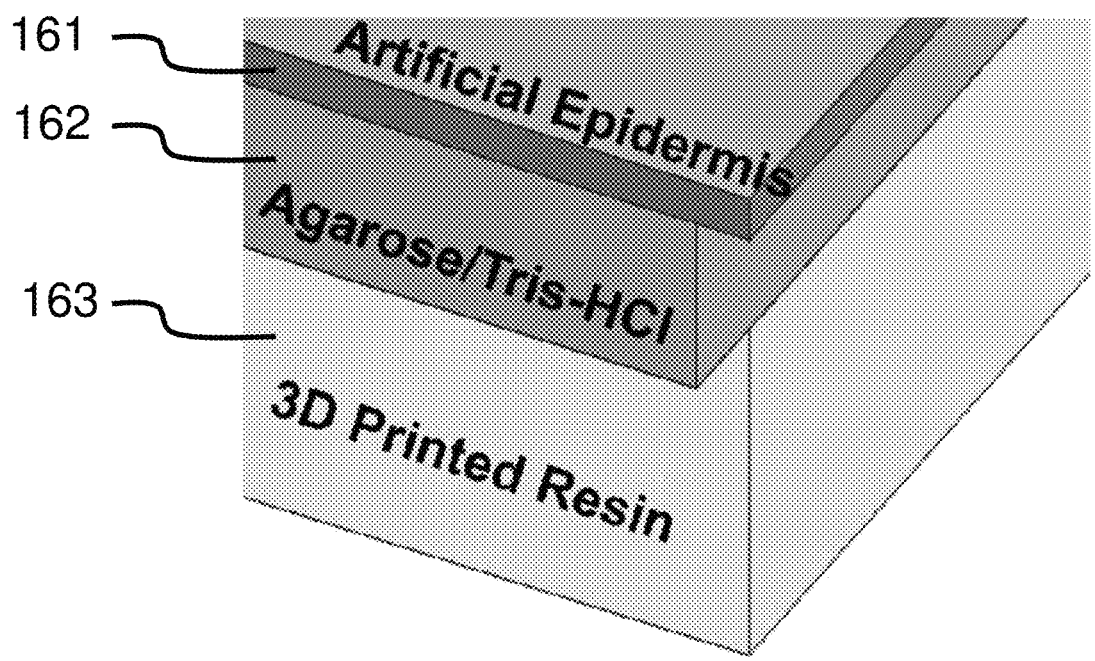
FIG. 16A: is an example according to various embodiments illustrating a schematic representation of the artificial skin model, in which element 161 represents an artificial, non-conductive epidermis patch, element 162 represents an agarose/Tris-HCl artificial dermis tissue, and element 163 represents a 3D printed mold accommodating the skin model.
Figure 16B:
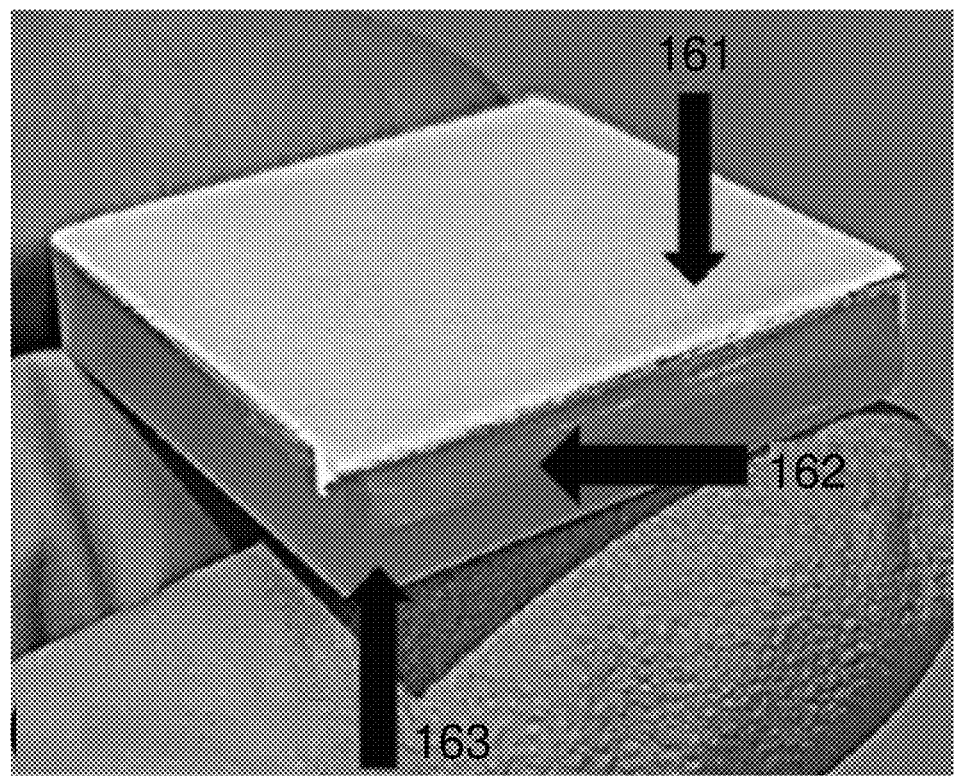
FIG. 16B: is an example according to various embodiments illustrating an optical image of the artificial skin model shown in FIG. 16A, with elements 161-163 corresponding to the schematic components listed with respect to FIG. 16A.

In order to demonstrate a wearable 3D MEA sensor application, highlighting the versatility of the microserpentine design structure, an artificial skin model was developed. FIG. 16A is an example according to various embodiments illustrating a schematic representation of the artificial skin model, in which element 161 represents an artificial, non-conductive epidermis patch, element 162 represents an agarose/Tris-HCl artificial dermis tissue, and element 163 represents a 3D printed mold accommodating the skin model. FIG. 16B is an example according to various embodiments illustrating an optical image of the artificial skin model shown in FIG. 16A, with elements 161-163 corresponding to the schematic components listed with respect to FIG. 16A. The agarose "dermal tissue" was cast in a custom 3D printed mold, and covered with a non-conductive epidermal layer, as is represented schematically in FIG. 16A, and optically in FIG. 16B. The surface DC resistance of the agarose "dermal tissue" model layer was found to be ~60 kΩ (+/−1.40 kΩ; N=3), and the end-to-end absolute resistance of the penetrated agarose was measured at 30 kΩ (+/−0.20 kΩ; N=3).

Figure 17A:
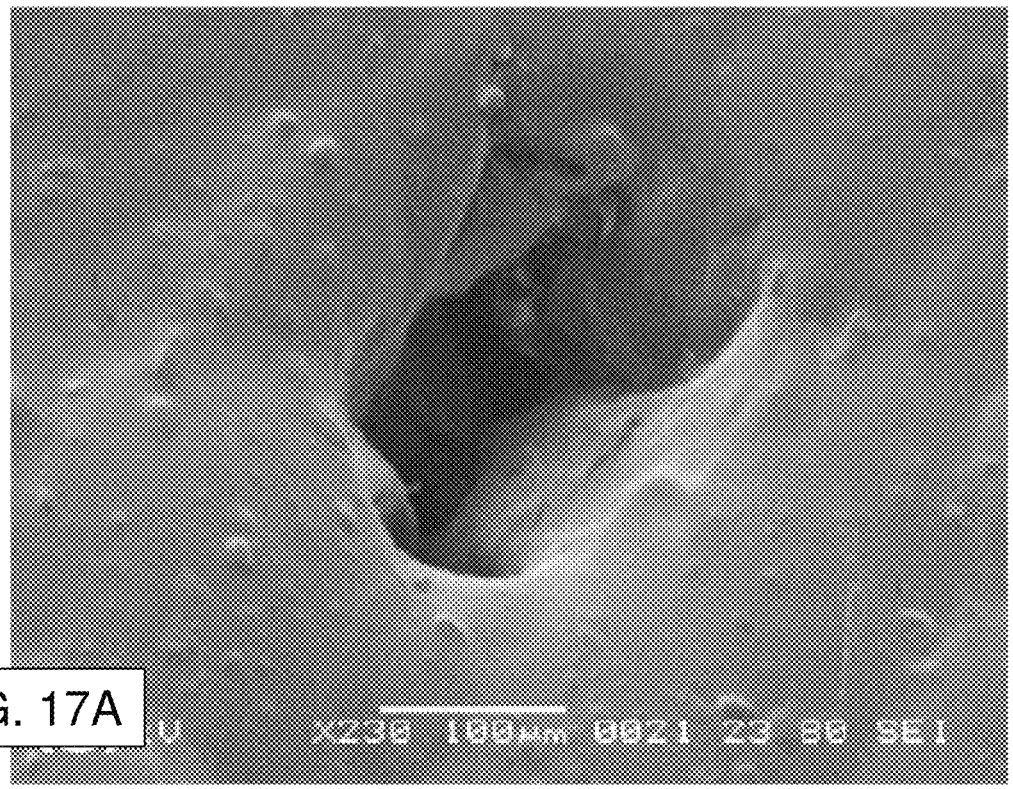
FIG. 17A: is an example according to various embodiments illustrating an SEM image of a puncture site on the artificial epidermis, demonstrating the feasibility of the 3D printed microneedle microelectrode towers to penetrate skin for potential transdermal/tissue recording applications.
Figure 17B:
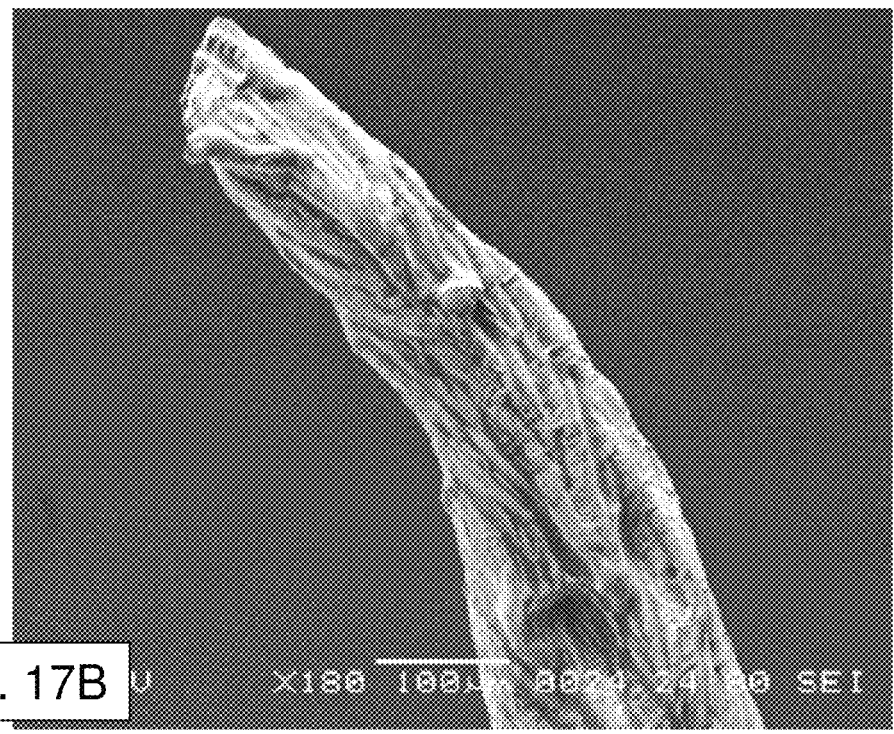
FIG. 17B: is an example according to various embodiments illustrating an SEM image of an electrode tip from one device which was not properly heat cured to give the resin its final robust structure, which is essential according to various embodiments to ensure that the resin electrodes are able to penetrate the skin or skin model.

FIG. 17A is an example according to various embodiments illustrating an SEM image of a puncture site on the artificial epidermis, demonstrating the feasibility of the 3D printed microneedle microelectrode towers to penetrate skin for potential transdermal/tissue recording applications. FIG. 17B is an example according to various embodiments illustrating an SEM image of an electrode tip from one device which was not properly heat cured to give the resin its final robust structure, which is essential according to various embodiments to ensure that the resin electrodes are able to penetrate the skin or skin model. The microserpentine device electrodes were interfaced with the artificial skin model to record sub-dermal tissue DC resistance to confirm the ability of the microelectrodes to penetrate the epidermis (FIG. 17A). The device successfully acquired a reading of the underlying tissue model, at DC resistances between 40 kΩ and 50 kΩ, across several puncture points in the model. The resistivity of the model according to the resulting DC resistance measurements was calculated to be ~50 Ω-m, well within expected values. Generally, the 3D printed resin structures require heat curing after printing, to ensure the full stability and rigidity of the fabricated structures. As depicted in FIG. 17B, there was some damage noted to certain microelectrode tips after pressing on the artificial skin model. These tips may not have been completely thermally cured (usually the curing time for other device components serves well for this purpose) but reducing the tower aspect ratio could also help increase their stability after shorter heat curing times. This proof of concept demonstration highlights the potential for these sensors to be used in wearable EEG, ECG, EMG and nerve conduction measurements.

Figure 18A:
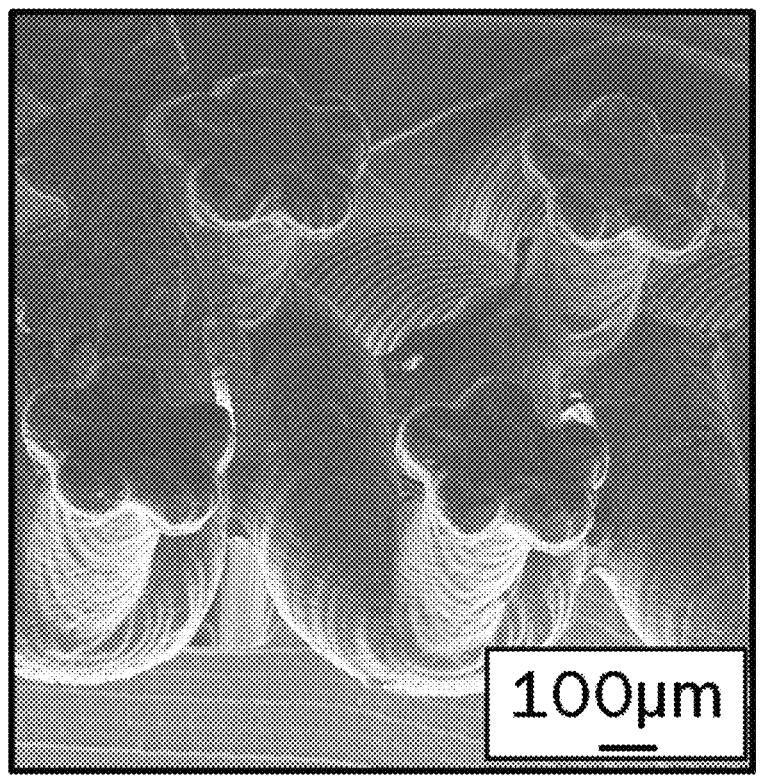
FIG. 18A: is an example according to various embodiments illustrating an SEM image of an alternative out of plane, monolithically integrated structures on a microserpentine, demonstrating the potential for another microsensor integrated out of plane from a microserpentines, more specifically μSLA 3D-printed cell surface adhesion promoters.
Figure 18B:
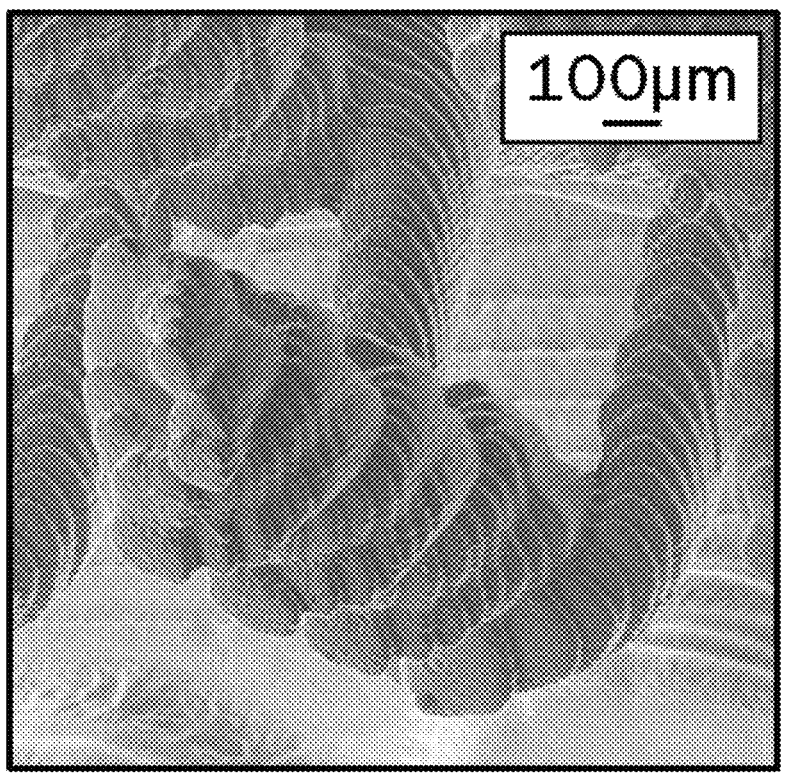
FIG. 18B: is an example according to various embodiments illustrating an SEM image of an alternative out of plane, monolithically integrated structures on a microserpentine, demonstrating the potential for another microsensor integrated out of plane from a microserpentines, more specifically μSLA 3D-printed microhelices.
Figure 18C:
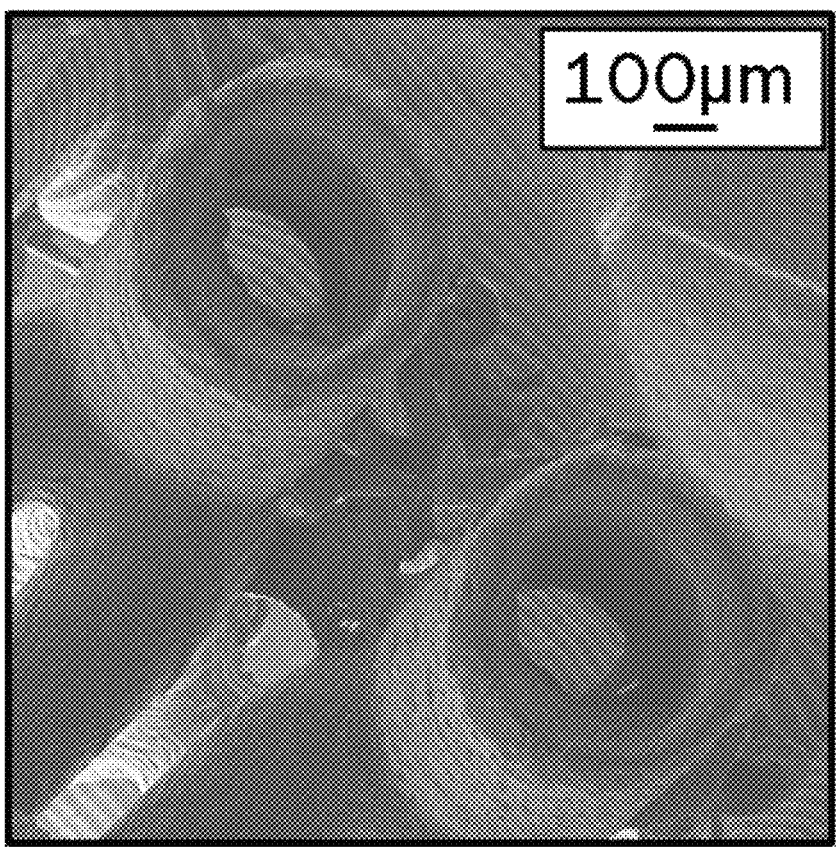
FIG. 18C: is an example according to various embodiments illustrating an SEM image of an alternative out of plane, monolithically integrated structures on a microserpentine, demonstrating the potential for another microsensor integrated out of plane from a microserpentines, more specifically μSLA 3D-printed microfluidic ports.
Figure 18D:
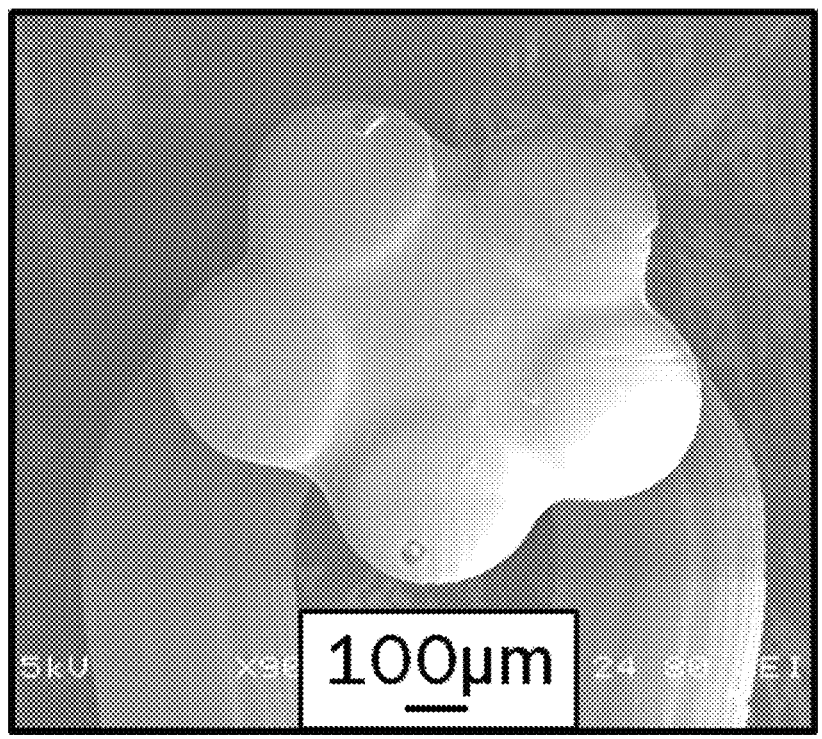
FIG. 18D: is an example according to various embodiments illustrating an SEM image of an alternative out of plane, monolithically integrated structures on a microserpentine, demonstrating the potential for another microsensor integrated out of plane from a microserpentines, more specifically 3D printed (on a DLP 3D printer) cell surface adhesion promoters.
Figure 18E:
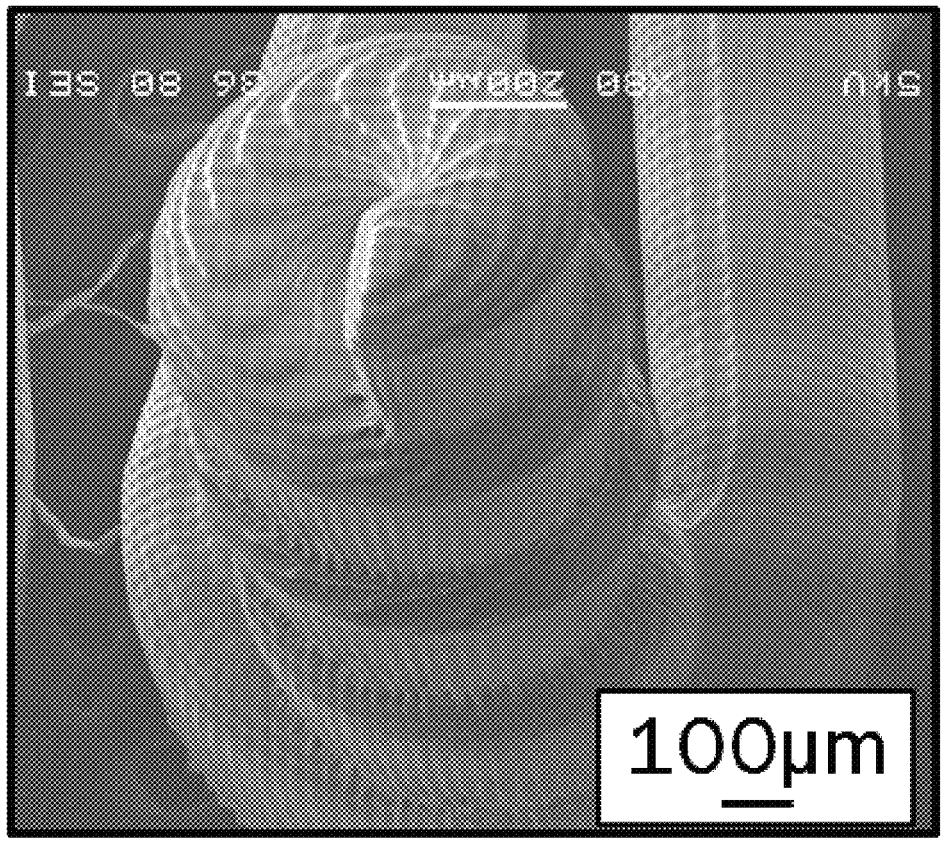
FIG. 18E: is an example according to various embodiments illustrating an SEM image of an alternative out of plane, monolithically integrated structures on a microserpentine, demonstrating the potential for another microsensor integrated out of plane from a microserpentines, more specifically microhelices.
Figure 18F:
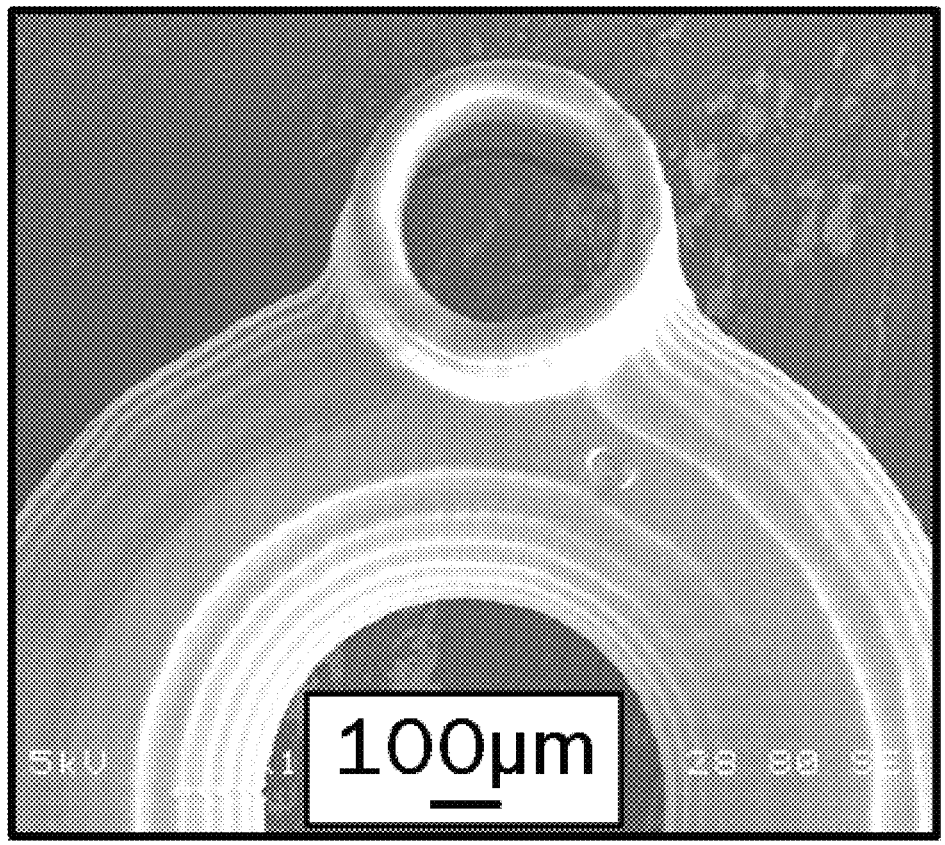
FIG. 18F: is an example according to various embodiments illustrating an SEM image of an alternative out of plane, monolithically integrated structures on a microserpentine, demonstrating the potential for another microsensor integrated out of plane from a microserpentines, more specifically microfluidic ports.
Figure 19A:
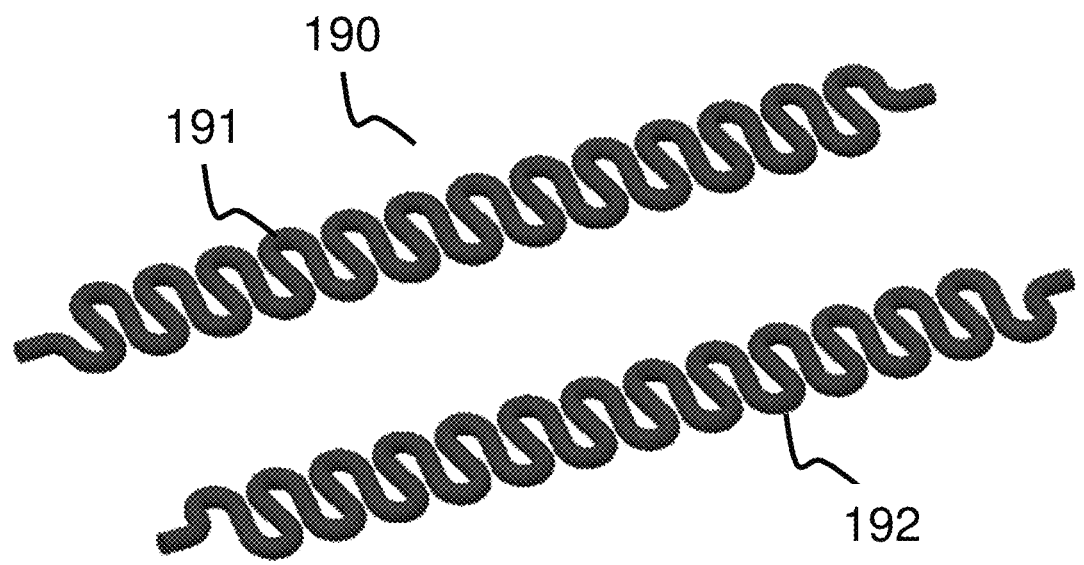
FIG. 19A: is an example according to various embodiments illustrating a schematic representation of one step of the production of a microserpentine μLED device, more specifically a schematic of a 3D printed double microserpentine conformation, where one microserpentine would correspond to the anode and one to the cathode of the device.
Figure 19B:
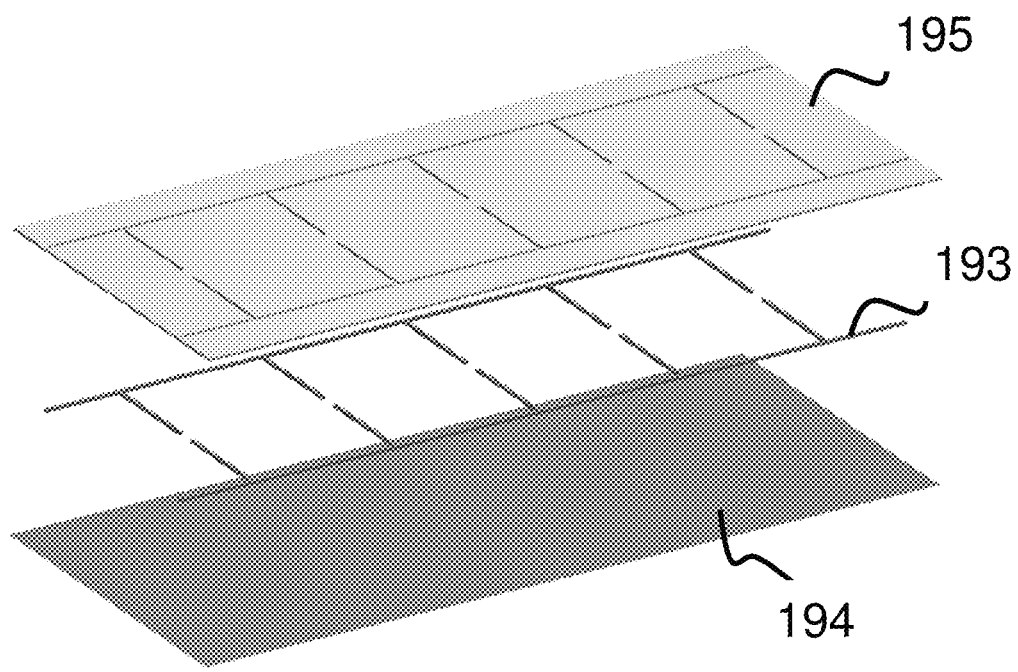
FIG. 19B: is an example according to various embodiments illustrating a schematic representation of one step of the production of a microserpentine μLED device, more specifically a schematic of the ink-casting process on a laser micromachined KAPTON® substrate.
Figure 19C:
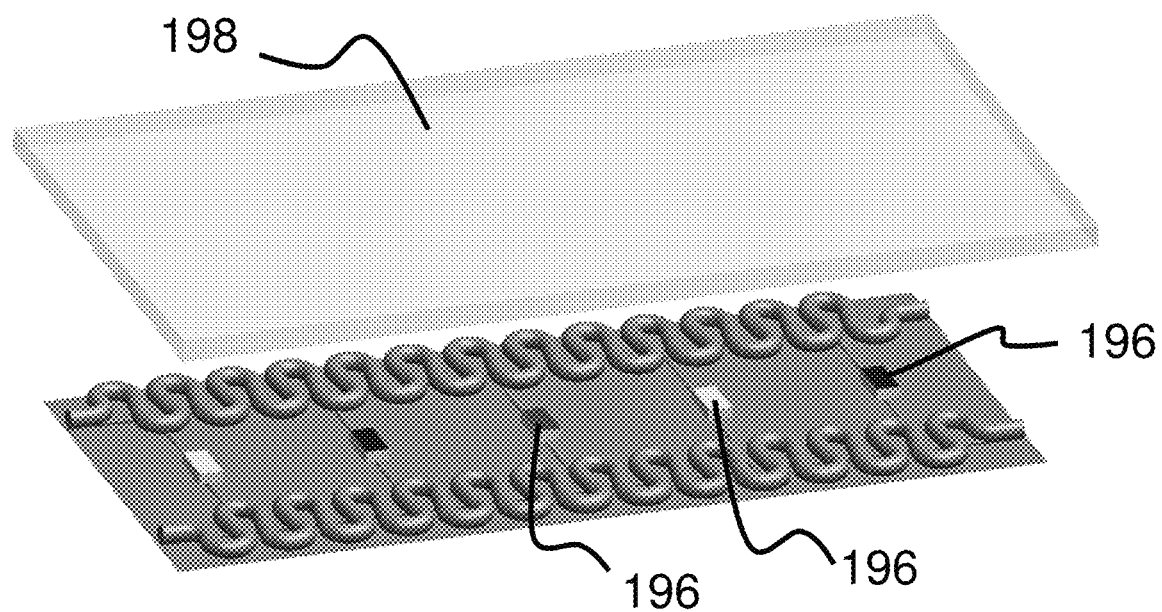
FIG. 19C: is an example according to various embodiments illustrating a schematic representation of one step of the production of a microserpentine μLED device, more specifically an assembly of the schematic device, illustrating the positioning of the two ink-coated microserpentines onto the substrate, the μLED addition, and the PDMS encapsulation.
Figure 19D:
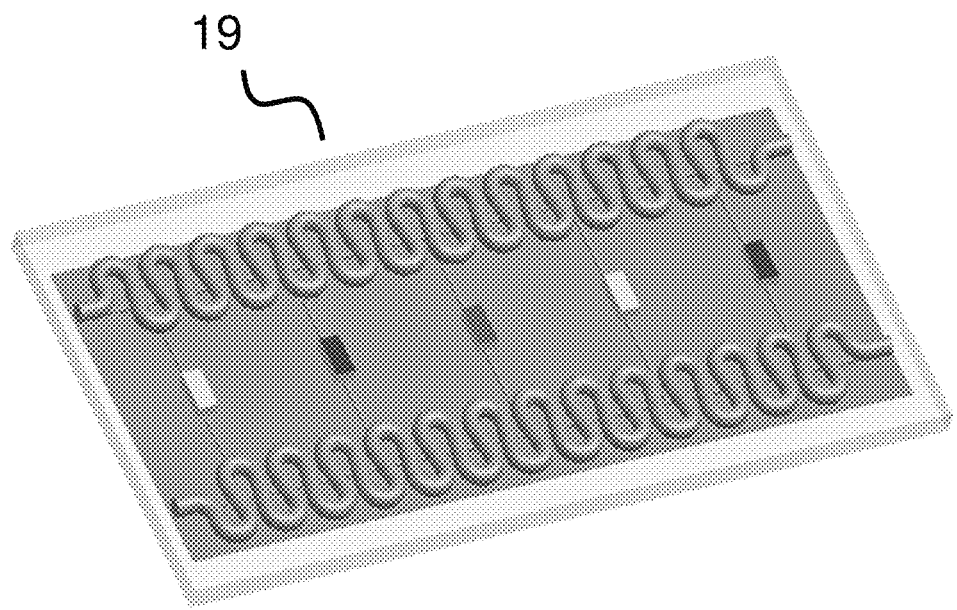
FIG. 19D: is an example according to various embodiments illustrating a schematic representation of one step of the production of a microserpentine μLED device, more specifically a schematic of the final fully assembled device.

The versatility which 3D printing imparts on the fabrication process, means that complex, arbitrarily defined 3D structures could be incorporated in the device, leading to a variety of potential lab-on-a-chip, wearable, and cell culture applications in areas such as microneedles, 3D microfluidics, cellular constructs and helices (FIGS. 18A, 18B, 18C, 18D, 18E, and 18F). FIG. 18A is an example according to various embodiments illustrating an SEM image of an alternative out of plane, monolithically integrated structures on a microserpentine, demonstrating the potential for another microsensor integrated out of plane from a microserpentines, more specifically μSLA 3D-printed cell surface adhesion promoters. FIG. 18B is an example according to various embodiments illustrating an SEM image of an alternative out of plane, monolithically integrated structures on a microserpentine, demonstrating the potential for another microsensor integrated out of plane from a microserpentines, more specifically μSLA 3D-printed microhelices. FIG. 18C is an example according to various embodiments illustrating an SEM image of an alternative out of plane, monolithically integrated structures on a microserpentine, demonstrating the potential for another microsensor integrated out of plane from a microserpentines, more specifically μSLA 3D-printed microfluidic ports. FIG. 18D is an example according to various embodiments illustrating an SEM image of an alternative out of plane, monolithically integrated structures on a microserpentine, demonstrating the potential for another microsensor integrated out of plane from a microserpentines, more specifically 3D printed (on a DLP 3D printer) cell surface adhesion promoters. FIG. 18E is an example according to various embodiments illustrating an SEM image of an alternative out of plane, monolithically integrated structures on a microserpentine, demonstrating the potential for another microsensor integrated out of plane from a microserpentines, more specifically microhelices. FIG. 18F is an example according to various embodiments illustrating an SEM image of an alternative out of plane, monolithically integrated structures on a microserpentine, demonstrating the potential for another microsensor integrated out of plane from a microserpentines, more specifically microfluidic ports. Using the fabrication process described in this work, and a printer with smaller minimum feature sizes (such as Nanoscribe or Asiga Digital Light Projection (DLP) printers), smaller functional electrodes could be manufactured, potentially extending various surface geometries into the nanoscale. The calculations used to optimize the printed microserpentines are ubiquitous due to the geometric nature of the key parameters of the device (I, R, w, α, etc.). However, practical design considerations, printing technique, and usability in packaged biosensor designs, control the characteristics microserpentines. FIG. 19A is an example according to various embodiments illustrating a schematic representation of one step of the production of a microserpentine μLED device 19, more specifically a schematic of a 3D printed double microserpentine conformation 190, where one microserpentine would correspond to the anode 191 and one to the cathode 192 of the device 19. FIG. 19B is an example according to various embodiments illustrating a schematic representation of one step of the production of a microserpentine μLED device 19, more specifically a schematic of the ink-casting process in which traces 193 are applied to a laser micromachined KAPTON® substrate 194 with assistance of a metal mask 195. FIG. 19C is an example according to various embodiments illustrating a schematic representation of one step of the production of a microserpentine μLED device 19, more specifically an assembly of the schematic device, illustrating the positioning of the two ink-coated microserpentines onto the substrate, the μLED addition 196, and the PDMS encapsulation 198. FIG. 19D is an example according to various embodiments illustrating a schematic representation of one step of the production of a microserpentine μLED device 19, more specifically a schematic of the final fully assembled device.

Figure 20A:
FIG. 20A: is an example according to various embodiments illustrating an optical image of the assembled and fabricated device, with μLEDs lighted under a concave bending conformation.
Figure 20B:
FIG. 20B: is an example according to various embodiments illustrating an optical image of the μLED device continuing to perform successfully even while twisted into a tight barrel conformation.

FIG. 20A is an example according to various embodiments illustrating an optical image of the assembled and fabricated device, with μLEDs lighted under a concave bending conformation. FIG. 20B is an example according to various embodiments illustrating an optical image of the μLED device continuing to perform successfully even while twisted into a tight barrel conformation.

Materials and Methods

Thin KAPTON® (12.5 μm) sheets (DuPont™, USA) were laser micromachined to a size of 20 mm by 5 mm, with 1 mm by 1 mm extensions (6 on either side of the base substrate; 12 total) on which the microelectrode landing pads would be subsequently defined (FIG. 2B). Laser micromachined shadow masks for were machined from 12.5 μm thick 316L stainless steel (Trinity Brand Industries, USA) using the QuikLaze 50 ST2 laser micromachining system (Eolite Lasers, USA) with 1064 nm wavelength Infrared (IR) laser light (6 mJ power, and 50 Hz repetition rate) (FIG. 2B). These masks served as stencils for subsequent metallization. Gold (5N, 57 mm by 0.2 mm Au target; Ted Pella, INC., USA) was deposited on the 3D printed substrate (Deposition voltage: 20 mV, and 13 nm/min deposition rate) to form 33 nm thick packaging traces and landing pads through the Quorum Q150T Plus sputtering system (Quorum Technologies Ltd., UK) (FIG. 2B).

The 3D microserpentines with and without out-of-plane biosensor structures were designed with Solidworks 2018 3D CAD software (Dassault Systems, USA) and 3D printed using commercially available clear (FLGPCL04) resins on the FORMLABS® Form 2 Micro-Stereolithography (μSLA) 3D printer (FORMLABS®, USA) (FIGS. 1A and 2A). The microserpentines were designed to be 400 μm thick, and the pitch between the central points of the U-bends varies between the three printed designs, which are shown in FIGS. 4A, 4C, and 4E. The $\alpha=0°$ design has a pitch of 1.5 mm; the $\alpha=-33°$ design has a pitch of 2.19 mm, and the $\alpha=10°$ design has a pitch of 1.3 mm (FIGS. 4A, 4C, and 4E). All out-of-plane 3D printed structures were designed to be 400 μm at the base and with a height of 2 mm. The physical printed electrode cones before insulation resolved at approximately 1.1 mm above the microserpentine U-bend, and so the resolved electrodes cones before insulation were 400 μm at the base, and 1.1 mm in height. The pitch between the 3D structures was designed to be 1.3 mm (similar to the $\alpha=10°$ design). The printed microserpentine was similarly metallized utilizing a sputter coater (Quorum Q150T Plus; Quorum Technologies Ltd., UK) with a layer of Gold (5N, 57 mm by 0.2 mm Au target; Ted Pella, INC., USA), under the same deposition rates as outlined above (20 mV, and 13 nm/min deposition rate) to form conformal coatings across the entire 3D microserpentine structure with thicknesses ranging from 7 nm to 70 nm (FIG. 2C). The microelectrodes on the microserpentines were isolated down the center (both front and backsides) of the structure using the QuikLaze 50 ST2 laser micromachining system (Eolite Lasers, USA) with 1064 nm wavelength IR mode (6 mJ power, and 50 Hz repetition rate), which selectively ablated the gold and did not damage the resin (FIG. 2C). For the microelectrode array design, the microserpentines were aligned with the terminated metal traces of the packaging substrate, and a small droplet of the EPO-TEK® EJ2189 silver-ink (Epo-Tech, USA) was placed on the microserpentines/trace interface to ensure connectivity. The package was cured for 24 hours at 45° C. (FIG. 2C).

A drop-casted layer of 10:1 PDMS bulk polymer to curing agent (Slygard-184, Dow Corning, USA) was defined as the final insulation layer on the 3D electrodes (FIG. 2C). A custom designed and 3D printed mold was developed to assemble the devices into their final form factor. PDMS was cast within this mold to ensure a uniform thickness across the device. The assembly mold was sputter coated with gold separation layer to a thickness of 70 nm, to ensure curing of PDMS, which was observed, to be inhibited by the resin. The thickness of the final PDMS insulation was defined and insulated at 1 mm thick (FIG. 2D). The device assembly were cured at 50° C. for an additional 24 hours to attain the full cross-linked mechanical properties of the PDMS.

Elongation experiments for microserpentines characterization were performed by clipping contacts to both ends of the microserpentines and recording the DC resistance measurements from a Keithley 2400 Sourcemeter (Tektronix, USA) (FIGS. 7A, 7B, 7C, 7D, 7E, and 7F; FIGS. 10A, 10B, 10C, and 10D; and FIGS. 11A, 11B, 11C, and 11D 6). Twisting/bending analysis, and hysteresis cycling were performed with tweezers under a stereoscope with wire leads epoxied to the landing pads for electrical characterization during the application of strain. Full spectrum impedance measurements were performed with a BODE 100 Impedance Analyzer (Omicron Labs, Austria) with a Platinum (Pt) anode in Dulbecco's Phosphate Buffered Saline (1×DPBS) (Gibco, USA) (FIGS. 15A and 15B). For SEM imaging of samples, the Zeiss Ultra-55 SEM (Zeiss, Germany) was used, and EDS was performed on the same SEM with the Noran System 7 EDS with Silicon Drift Detector X-ray Detector (Thermo Fisher Scientific, USA) (FIGS. 3A-B, 4A-F, 5, 6A-C, 8A-D, 9A-F, 13A-13D, 14A-C, 15A-D, 16A-B, and 17A-B). All optical images were obtained with an iPhone XS (Apple, USA). Data graphing was performed in Origin 2016 (OriginLab Corporation, USA). Data fitting and impedance modelling were performed in MATLAB R 2018b (Mathworks, USA). Effective stiffness and normalized maximum tensile strain calculations were defined and implemented with appropriate design values using Wolfram Mathematica 11.3 (Wolfram, USA) (FIGS. 3A and 3B). The Agarose dermal tissue model was created from a 1M solution of Tris-HCl (pH 6.1), and powdered agarose. The mixture was placed in a beaker and stirred continuously to a boil of 100° C. on a hotplate. According to the references, 3 mm thick agarose mixed in the aforementioned protocol, models' dermal tissue closely, with a conductivity of 0.06 S/m. The agar was poured into a custom 3D printed 25 mm by 25 mm mold (3 mm thick as per the protocol from these papers) and allowed to fully crosslink at 25° C. for an hour. The epidermis was modelled with an artificial, 500 μm thick epidermal patch (Remedy Simulation Group, USA), and attached to the mold/agarose dermis with integrated adhesive. The artificial epidermal patch is non-conducting, to model an enhanced effect of the dead skin layer of the stratum corneum present in real epidermal skin layers. 3D Microelectrode Arrays (depicted in FIG. 13A) were pressed onto the epidermis/dermis skin model and DC resistance values were obtained from the 3D electrodes across the device using a Keithley 2400 Sourcemeter (Tektronix, USA) (FIG. 16B).

What is claimed is:

1. A microserpentine comprising a plurality of u-bends, each having a degree of completeness ($\alpha$), wherein an $\alpha$ value of 0° corresponds to a semi-circular shape, and wherein an $\alpha$ value of +90° corresponds to a complete circle and −90° corresponds to a straight shape, the microserpentine comprising a plurality of out of plane electrode structures;

wherein each of the plurality of u-bends has an $\alpha$ value of from about 5° to about 15°, and wherein the microserpentine comprises a core comprised of a polymeric material coated with a conductive coating.

2. The microserpentine according to claim 1, wherein the microserpentine has an average length (l) between each of the plurality of u-bends, wherein each u-bend has an average radius (R), and wherein the ratio of l to R (l/R) is about 2.

3. The microserpentine according to claim 1, wherein the microserpentine is stretchable to about 155% its resting length.

4. The micro serpentine according to claim 1, wherein the polymeric material comprises one selected from a methacrylate-based polymer, a urethane-based polymer, a styrene-based polymer, a siloxane-based polymer, a nitrile-based polymer, a block co-polymer, a hydrogel-based polymer, a fluoro-elastomer-based polymer, and combinations thereof.

5. The microserpentine according to claim 1, wherein the conductive coating comprises one selected from a metallic material, a conductive polymer, a conductive polymer composite, and combinations thereof.

6. The microserpentine according to claim 1, wherein the conductive coating comprises a metallic material selected from gold, palladium, titanium, magnesium, zinc, platinum, and combinations thereof.

7. The microserpentine according to claim 1, wherein the conductive coating is about 5 nm to about 300 µm thick.

8. A microelectronic device comprising a microserpentine according to claim 1.

9. The microelectronic device according to claim 8, wherein the microelectronic device is selected from a microelectrode array, a microelectronics packaging, an interconnect, a stretchable sensor, a wearable sensor, a wearable actuator, an in vitro sensor, an in vivo sensor, and combinations thereof.

* * * * *